United States Patent [19]
Franklin et al.

[11] Patent Number: 6,130,253
[45] Date of Patent: *Oct. 10, 2000

[54] TERPENE BASED PESTICIDE TREATMENTS FOR KILLING TERRESTRIAL ARTHROPODS INCLUDING, AMONGST OTHERS, LICE, LICE EGGS, MITES AND ANTS

[75] Inventors: Lanny Udell Franklin, Atlanta, Ga.; Gary David Cunnington, Long Wittenham; David E. Young, Watlington, both of United Kingdom

[73] Assignee: XiMed Group PLC, Didcot

[*] Notice: This patent is subject to a terminal disclaimer.

[21] Appl. No.: 09/379,268

[22] Filed: Aug. 23, 1999

Related U.S. Application Data

[63] Continuation-in-part of application No. 09/151,973, Sep. 11, 1998, Pat. No. 5,977,186.
[60] Provisional application No. 60/072,775, Jan. 27, 1998.
[51] Int. Cl.$^7$ .......................... A01N 27/00; A01N 31/02; A01N 31/08; A01N 35/02; A01N 35/06
[52] U.S. Cl. .......................... 514/690; 514/692; 514/698; 514/703; 514/717; 514/720; 514/733; 514/739; 514/762; 514/763; 514/875; 514/880; 514/881; 514/944; 514/970; 510/382; 510/386
[58] Field of Search ..................................... 514/690, 733, 514/739, 762, 763, 875, 880, 881, 692, 698, 703, 717, 720, 944, 970; 510/382, 386

[56] References Cited

U.S. PATENT DOCUMENTS

| | | | |
|---|---|---|---|
| 4,927,813 | 5/1990 | Bernstein | 514/65 |
| 4,933,371 | 6/1990 | Hink et al. | 514/739 |
| 5,411,992 | 5/1995 | Eini et al. | 514/731 |
| 5,591,435 | 1/1997 | Vaccarello-Dunkel et al. | 424/195.1 |
| 5,610,189 | 3/1997 | Whiteley | 514/557 |
| 5,627,166 | 5/1997 | Iwasaki | 514/78 |
| 5,635,174 | 6/1997 | Warren et al. | 424/84 |
| 5,653,991 | 8/1997 | Rod | 424/406 |
| 5,693,344 | 12/1997 | Knight et al. | 424/687 |
| B1 4,379,168 | 1/1990 | Dotolo | 514/763 |

OTHER PUBLICATIONS

BMJ Nov. 18, 1995; 311 (7016):1369; discussion 1369–70. Comment in : BMJ Jan. 13, 1996; 312 (7023); discussion 123.

Vander Stichele R.H. et al. Systematic review of clinical efficacy of topical treatment for head lice. BMJ Sep. 2, 1995. p604–8.

Price Ja, et al. Measurement of airborne mite antigen in homes of asthmatic children. *Lancet* 1990; 336:895–897.

Sporik R, et al. Exposure to house–dust mite allergen (Der p 1) and the development of asthma in childhood. A prospective study. *N Engl J Med* 1990; 323:502–507.

Platts–Mills Ta, et al. Reduction of bronchial hyperreactivity during prolonged allergen avoidance, *Lancet* 1982; 2:675–678.

Platts–Mills Tae, de Weck Al. Dust mite allergens and asthma—a worldwide problem. *J Allergy Clin Immunol* 1989; 83:416–427.

Platts–Mills Ta, et al. Dust mite allergens and asthma: report of a second international workshop. *J Allergy Clin Immunol* 1992; 89:1046–1060.

Sporik R. Chapman MD, Platts–Mills Ta. House–dust mite exposure as a cause of asthma. *Clin Exp Allergy* 1992; 22:897–906.

Platts–Mills Tae, et al. Role of allergens in asthma and airway hyperresponsiveness: relevance to immunotherapy and allergen avoidance, in Kaliner MA, Barnes PJ, Persson CGA (eds), *Asthma: Its Pathology and Treatment*. New York, Marcel Dekker, 1991, ch 22.

*Primary Examiner*—John Pak
*Attorney, Agent, or Firm*—Tilton, Fallon, Lungmus & Chestnut

[57] ABSTRACT

Pesticides for the extermination of terrestrial arthropods are disclosed which comprise formulations of a combination of terpenes in aqueous solutions which may be used together with citral. No resistance to the formulations of the invention has been seen. When used on the scalp or body for lice infestation no extended dwell time is required. The formulations do not have unpleasant odors. The formulations are directed towards providing topical preparations which may be used on the skin, scalp and hairy body parts of humans and animals, sprays for use directly against terrestrial arthropods, a dipping solution for combs and a laundry additive, amongst others.

42 Claims, No Drawings

TERPENE BASED PESTICIDE TREATMENTS FOR KILLING TERRESTRIAL ARTHROPODS INCLUDING, AMONGST OTHERS, LICE, LICE EGGS, MITES AND ANTS

REFERENCE TO RELATED APPLICATIONS

This application is a Continuation-in-Part of U.S. application Ser. No. 09/151,973, filed Sep. 11, 1998, now issued as U.S. Pat. No. 5,977,186 which was entitled to the benefit of the filing date of U.S. Provisional Application No. 60/072,775, filed Jan. 27, 1998.

FIELD OF THE INVENTION

This invention is concerned with the control of pest infestation of man, animals and their environment by terrestrial arthropods. The invention is a group of pharmaceutical formulations comprising a combination of terpenes, together with citral. The selected terpenes when mixed, with or without citral added, have been found to be highly effective, in aqueous solutions, in killing lice and their eggs, ants, mites and other parasites. The principal mode of action on adults and larvae is by direct solvent action on the wax-containing epicuticle of the chitinous exoskeleton, which is the primary means of controlling water loss in terrestrial arthropods.

BACKGROUND TO THE PRESENT INVENTION AND THE PRIOR ART

Pediculosis (lice infestation) in humans has been known since ancient times. Lice infestations are common throughout the world. In the United States alone, an estimated ten million cases of pediculosis occurred during 1985 and the numbers have increased substantially since then. In Europe, lice infestation has reached epidemic proportions.

Three types of lice infest humans: 1) head lice, 2) body lice and 3) crab or pubic lice. All are members of the family Pediculidae and most are species within the genus Pediculus. They are small, flat, grayish-black, wingless insects. Their six legs are short and stout, with a large claw on each leg for grasping and holding onto hair. They have piercing and sucking mouth parts for blood feeding and require close contact with human hosts, to which they are very well adapted. The three types differ considerably in habitat and to a small degree, in their life cycles. Lice also infest domestic, farm and wild animals.

*Acarine arachnids*, or mites, have a serious effect upon man and his environment. House dust mites are the main causative agent of exacerbations of one of the worst ailments of twentieth-century man—asthma. Mites and ticks can carry serious pathogens which threaten man and cause morbidity in livestock. Psoroptid mites produce mange in both farm and domestic animals and sarcoptid mites cause much suffering and discomfort through scabies. Mites also infest many crop plants.

Other insects, whether directly parasitic upon man and his animals or by virtue of infesting the human environment in large numbers, can cause much hardship and destruction. Amongst many species which cause such problems are ants.

Terpenes are bio-active compounds and there are numerous reports in the literature concerning their effects as antibacterial, antifungal, antihelminthic and antimitotic agents. Various terpenes are used in agriculture for growth inhibition, growth promotion and in the food industry as flavorings and fragrances. Interest in the potential for using terpenes in medical applications is increasing.

Citral is a component of certain essential oils, in particular lemongrass (*Cymbopogon citratus*), and is typically produced by steam distillation. It can also be produced synthetically. It is a terpene aldehyde with the molecular formula $C_{10}H_{16}O$ and has a molecular weight of 155.24. It is known to have limited antibacterial and anti-fungal effects.

LICE

Lice have three stages in their life cycle: egg, nymph (young) and adult. Newly hatched nymphs are identical in appearance to their parents except for the second instar (nymph) which is smaller and has undeveloped reproductive organs. Nymphs gradually develop into adults, periodically shedding their skin (molting) during the process. The life cycle (egg to egg) takes approximately 15 to 35 days, during which time a female may lay between 50 and 150 eggs. Lice spend their entire life as ectoparasites on humans and, unlike other insects, have a relatively consistent environment. Their close contact with human skin ensures favorable temperatures of 82° F. to 88° F., and an abundant food supply. Lice do not abandon their hosts unless the body temperature substantially changes due to death or high fever. Once dislodged from a person's body or clothing, they will infest a new human host in the immediate proximity. If a new host is not found within a few hours to eight days, according to species, lice will starve to death.

During feeding, lice inject saliva into the skin of the host and this causes irritation and subsequent itching. Children under 12 years are more sensitive to louse feeding than other age groups. Scratching louse bite areas frequently causes an abrasion, which may become infected with other microorganisms. Prolonged louse infestation causes a hardening and pigmentation of the skin known as "Vagabond's Disease".

Even though people experience unpleasant sensations as a result of louse infestation, they often deny pediculosis because of feelings of disgust and shame. Lice infestation used to be thought of as a problem only of the poor or poorly housed. It is now abundantly clear that the problem of head lice has extended to a very large number of middle class homes in the western world and this leads to increasing numbers of consultations with family practitioners or pharmacists who advise as to the treatment currently being recommended.

Lice are spread through sharing contaminated clothing, hats, scarves, combs, hair brushes, and other headgear, or as a result of close physical contact with an infested person. Other occasional sources are bedding, furniture, rugs and floor surfaces where dislodged lice may be present.

Once infested, an individual usually carries a few dozen lice. However, some people have been known to carry several hundred lice and, on rare occasions, one to two thousand lice. Human lice do not normally infest pets and domestic animals.

Of the three species of lice, only body lice have been known to transmit disease organisms. Relapsing fever, typhus and trench fevers were transmitted by body lice in Europe during World Wars I and II and the Naples Typhus Epidemic of 1944 was brought under control using DDT to kill lice—one of the earliest widespread uses of this insecticide.

Head lice (pediculosus humanus capitus) are by far the most common and troublesome of the human lice infestations and, in the U.S. alone, between 8 and 12 million children have head lice at any one time.

"Nits" is the term used to describe the small yellowish-white, oval-shaped eggs cases of head lice that are 'glued' at an angle to the side of a hair shaft near its base. Favorite sites are behind the ears or on the nape of the neck. Eggs are laid by a mature female louse and after hatching feeding starts immediately. This activity causes the young head lice to rapidly develop a reddish-brown color. Development takes about 18 to 20 days and the adults can live for about one month, during which time each female lays between 50 and 150 eggs at the rate of four to six per day, usually at night. The eggs are cylindrical, yellowish-white and about 0.8 mm long. Feeding occurs at fairly frequent intervals and at least twice daily. The adult male is about 2.1 mm long and the female rather larger, about 3 mm long. Mating occurs within 10 hours of maturation and recurs quite frequently during the remainder of life. Head lice can survive three to four days if dislodged from the host.

Head lice are transferred from one infested person to another through physical contact and the communal use of combs, hair brushes, head apparel, towels, bedding, and personal clothing.

Feeding activity irritates the scalp, causing intense itching. Head lice are not known to transmit any disease organisms directly but a secondary infection may result if the skin is broken by repeatedly scratching the area. In severe infestations the hair may become matted as a result of exudates from louse bites.

The impact of being publicly identified as having lice (for instance in a school classroom) can be distressing and socially embarrassing. Children, particularly those of primary/first school age, are most likely to get head lice because of their close contact and social interactions with each other, which creates numerous opportunities for lice to be spread amongst them. Children who become infested in school will carry lice home and may infest family members who unknowingly become a source for recurring louse problems in the home. Few parents react with total equanimity to the discovery.

The body louse or cootie (pediculosus humanus humanus), is very similar to the head louse in physical appearance except that it is 10% to 20% larger. This insect is generally associated with unclean environments where inadequate bathing occurs or clothes are shared. The body louse lives on clothing that comes in close contact with the human body, such as the waistline and crotch of trousers, shirt armpits and collars and underwear, rather than the body itself which it visits only to obtain a blood meal.

The life cycle of the body louse is, in many respects, similar to that of the head louse. However, in this louse, the fertilized female adult lays nine to ten eggs per day, and may lay 270 to 300 eggs in her lifetime. The eggs are usually glued to fibers of clothing, often in the seams. Eggs hatch in six to nine days. Newly hatched nymphs begin to suck blood at once and feed frequently during day or night, especially when the host is quiet. Nymphs mature to adults in approximately 16 to 18 days, during which process three moltings occur. Newly emerged adult males, 2.3 mm long, and females, 4.2 mm long, mate within a day. The female begins laying eggs one or two days after reaching maturity. The life cycle (egg to egg) is completed in 22 to 28 days. The adults are grayish white and live approximately 30 to 40 days. After discontinued contact with the host, body lice can survive eight to ten days. They spread through contact with infested persons or their clothing.

The crab or pubic louse has a crab-like appearance and is grayish white. Although formerly grouped within the genus Pediculus they are now more correctly classified as *Pthirus pubis* (syn. *Pediculus pubis*). They infest the pubic region of the body but in severe infestations may be found in armpits, moustaches, beards, eyelashes and eyebrows.

Fertilized adult females lay three eggs per day and a total of about 26 eggs in their lifetime. The oval, whitish eggs, 1/50 inch long, are glued to coarser hair near the skin. The eggs hatch after six to eight days. The newly hatched nymphs start sucking blood immediately. The nymphs grow into adults after molting three times in 15 to 17 days. The life cycle (egg to egg) is completed in 34 to 41 days. The adults are 1.6 mm long and live for a month on the human host. If they are dislodged, they survive less than 24 hours.

Both nymphs and adults tend to settle on one spot, and feeding continues intermittently for hours or days. Spread is through intimate physical contact, particularly sexual contact and possibly also through infested bedding, clothing and toilet seats.

In theory, elimination of head lice in an infested family should be relatively straightforward. Advice is readily available in schools and GP surgeries in Western countries. Reporting to school authorities is strongly encouraged but many parents evade the issue because of shame or embarrassment. Failure to report, coupled with lack of awareness that the problem exists or reluctance to deal with it at all, are the primary reasons for re-infestation in the school and community environments. Trained school staff, especially a nurse if there is one, do carry out inspections but often encounter difficulties with parents who adopt a state of denial.

The extent of delousing activities in a school depends on a variety of factors such as the age of the students and general resources. Difficult schools in inner city areas are particularly prone to the problem and have, in general, the least resources and also the least cooperative parent population. It is rare for schools, other than some residential schools, to treat head lice infestation actively. Once infestation is recognized in a group, the classic steps are to encourage inspection of the whole group and all of their family members, to encourage higher standards of personal hygiene and to institute pesticide treatment with chemicals. This tends to be applied as a lotion or conditioner which must be left for a specified dwell-time to be effective. The use of special combs which can remove both live lice and their eggs is also encouraged. The action of combing correctly is considered to help the problem by breaking the legs of the lice. It is also being recommended that hair is over-conditioned with a standard product as this makes it difficult for the lice to grip the hair shaft. In the case of pubic lice, transmitted by sexual contact, it is particularly important that the sexual partner(s) should be treated simultaneously to avoid re-infestation. Other general recommendations include machine washing in hot water (over 54° C.) or dry cleaning all clothing, including coats, hats, scarves, pillow cases, towels and bedding materials, which may have contacted an infested individual.

Most medicated shampoos and lotions for treating head lice are available over the counter, though some require a prescription. Widely used products in the OTC category in the U.S.A. include Rid Lice Killing Shampoo (Pfizer), Nix® Creme Rinse and A-2000 Shampoo Concentrate which contain pyrethrins and piperonal butoxide as the active ingredients (Al).

Prescribable U.S. brands include Kwell®, (containing lindane 1%, as the active ingredient) and Ovidem®, (active ingredient 0.5% malathion).

In the U.K. the treatments for lice have recently received negative press attention (Sunday Times, Oct. 5th 1997 and World In Action, documentary TV program, Channel 3, Independent Television) and, despite the fact that the press focussed on malathion (Derbac-M™, Prioderm™ and Suleo-M™; marketed in the U.K. by Seton Scholl Healthcare), there has been a domino effect and lice products generally are being increasingly thought of with caution. The key concerns are regarding the use of organophosphates and their associated toxicity, especially as they are so often used in young children. Malathion toxicity includes nausea, vomiting, diarrhea, broncho-constriction, blurred vision, excessive salivation, muscle twitching, cyanosis, convulsions, coma and respiratory failure. Against this background it may be somewhat surprising that its topical use was not more closely monitored earlier. Even permethrin (the active ingredient in Lyclear™) has to be used with caution and must not be used in an enclosed space. Products containing this active ingredient must also be kept away from pets and fish because of known direct toxicity in those species.

Pediculicides selectively kill lice which invade the epidermis. Although a number of brands contain either carbaryl or malathion, lotions containing phenothrin and permethrin are now the major products. These are pyrethroid compounds and are effective insecticidal neurotoxins, with efficacy against both adult lice and their eggs. Permethrin (3-phenoxyphenyl) methyl (+/−) cis/trans 3-(2,2-dichloroethenyl) 2,2-dimethylcyclopropanecarboxylate, is used as a 0.5% preparation in a paraffin base. Other active ingredients are benzyl benzoate and crotamiton. All are applied topically. The manufacturers claim appropriate use does not lead to resistance but evidence now to hand would seem to suggest otherwise. Indeed, local U.K. health authorities (through directives issued to GPs, school nurses and health visitors) advise alternation of products within a co-ordinated national policy. Many health authorities are now advising no active treatment because of problems apparently due to resistant lice. Instead they recommend over-conditioning the hair and regular use of a specially designed lice comb.

The main brands used in the U.K. are Lyclear™ Creme Rinse (Warner Lambert)—a lotion conditioner applied after shampooing and left for ten minutes and Full Marks™ (phenothrin—Seton Scholl Healthcare)—a lotion rubbed into the hair and left for two hours. These two products are prescribable but are also available over-the-counter. Lyclear™ appears to be the clear market leader. All prior art anti-head lice preparations have the drawback of requiring significant dwell-times on the scalp and this is negative for the products because it reduces user-compliance and encourages misuse. Both tendencies reduce the success rate in clearing lice. Manufacturers claim that resistance is not an issue and that treatment failures are due to incorrect use. However, this does clearly indicate that these agents are not user friendly.

The issue of efficacy of prior art preparations, used to control head lice, is important and in this context, a report by Van der Stichele R. H. et al, from the Heymans Institute of Pharmacology, University of Ghent, Belgium, entitled 'Systematic Review Of Clinical Efficacy Of Topical Treatments For Head Lice' (BMJ Sep. 2, 1995. p604–8), is relevant. The group sought to collect and evaluate all trials on clinical efficacy of topical treatments for head lice. They undertook a systematic review of randomized trials identified from the data sources Medline, International Pharmaceutical Abstracts, Science Citation Index, letters to key authors and companies and hand search of journals. All the trials reviewed were carried out in schools or communities in patients infested with lice. The main outcome measure, which the Review Group were concerned with, was cure rate (absence of live lice and viable nits) on day 14 after treatment. A total of 28 trials were identified and evaluated according to eight general and 18 lice-specific criteria. Of the 14 trials rated as having low to moderate risk of bias, seven were selected because they used the main outcome measure. These seven trials described 21 evaluations of eight different compounds and placebo (all but two evaluations were of single applications). Only permethrin 1% creme rinse showed efficacy in more than two studies with the lower 95% confidence limit of cure rate above 90%. The author's conclusion was that "only for permethrin has sufficient evidence been published to show efficacy. Less expensive treatments such as malathion and carbaryl need more evidence of efficacy. Lindane (1,2,3,4,5,6-Hexachlorocyclohexane) and the natural pyrethrins are not sufficiently effective to justify their use". In addition, many health authorities and registration agencies regard lindane, which is used as a scabicide, pediculicide and insecticide, as dangerous. It is tempting to speculate that the mechanism of resistance might be similar to that which arise with certain bacteria—a sublethal dose is repeatedly administered and engenders acquired resistance.

In the U.S.A. there are also products available for treating bedding, clothing and furniture including Lice Treatment Kit™ (active ingredient: resmethrin 0.5%), R & C Spray™ (active ingredient: phenothrin 0.382%) and Rid® Lice Control Spray (active ingredient: permethrin 0.5%). These products are available from stores rather than pharmacies and, so far as is known, there are no equivalent products available in the U.K.

Thus there is a significant need for a treatment for this widespread and troublesome problem that would address the issues which detract from the prior art products. An ideal product might offer no dwell time in excess of that for ordinary shampoos used by non-infested individuals, absence of toxicity, user friendly presentation and resistance-free mode of action.

The following U.S. patents are considered relevant: U.S. Pat. No. 5,635,174; U.S. Pat. No. 4,927,813; U.S. Pat. No. 4,379,168;U.S. Pat. No. 5,411,992; U.S. Pat. No. 5,591,435; U.S. Pat. No. 4,933,371; U.S. Pat. No. 5,627,166.

Other documents considered relevant are:

BMJ Nov. 18, 1995 ; 311(7016):1369 discussion 1369–70 incl Burgess, 1.

Mumcuogluo et al. Permethrin resistance in the head louse *Pediculosis capitis* from Israel. *Med Vet Entomol* 1996.

Rupes V, et al. A resistance of head lice (*Pediculosis capitis*) to permethrin in Czech Republic. *Centr Eur J Pub Health* 1995;3:30–2

Comment in: *BMJ* 1996 Jan 13;312 (7023): discussion 123.

Co-operative Extension, Institute of Agriculture and Natural Resources, University of Nebraska, Lincoln.

Larousse Encyclopaedia of Animal Life

Van der Stichele R. H. et al. Systematic review of clinical efficacy of topical treatments for head lice. *BMJ* Sep. 2, 1995. p604–8.

HOUSE DUST MITES

World-wide, dust mites are the main causative agent of exacerbations of one of the worst ailments of twentieth-century man—asthma. There has been an increasing prevalence of mite-related asthma in both adults and children, not only in the developed countries but also in the Asia Pacific region. The presence of domestic mites has been confirmed on a world-wide basis and the World Health Organisation has recognized domestic mite allergy as a universal health problem.

These mites are about 0.25 mm to 0.33 mm long and are thus not readily visible to the naked eye. The male is slightly smaller than female. They are whitish in color and thus can sometimes be visually detected in dust samples when they are moving on a dark background.

Mites are arthropods and have eight legs, no eyes, no developed respiratory structures and have been described as being a "volume which is mainly a walking stomach and respiratory system".

Mites are one of the oldest terrestrial animals, fossils having been found in deposits from the Devonian era (*Protacarus crani*). Today there are more than 45,000 species organized in 1700 genera. Those mites linked to asthma are present in large numbers in domestic household dust. Adult House Dust Mites *Dermatophogoides pteronyssinus* mites produce about 20 pelleted excreta per day. That house dust might contain allergens causing asthmatic symptoms was first suggested in 1921. However, analysis of dust was not satisfactorily accomplished until 1964, when a group of investigators led by Voohorst, suggested that a mite may be responsible for dust allergen. The results of this and subsequent studies identified a series of mite species which showed variable distribution between homes, between rooms within any given home and between different types of soft furnishings. Their ability to survive and thrive depends on the richness of their diet and suitability of temperature together with the relative humidity of their habitats. In general, humid homes have more mites and are, therefore, more rich in allergen. Optimum conditions for growth are a temperature between 22° C. and 26° C. and a relative humidity greater than 55% (or an absolute humidity less than 8 g/kg). House dust is composed of several organic and inorganic compounds, including fibers, mold spores, pollen grains, insects and insect feces, mammalian dander and mites and mite feces. It was soon established that mite fecal pellets become airborne following domestic activities such as vacuuming or dusting. Humans inhale these particles and this elicits allergic reactions in individuals who have a condition known as atopy. Atopy is a form of hypersensitivity response by the whole body to common, everyday particles which results in increased levels of the allergic antibody protein IgE in the blood circulation and tissues. Both atopy and asthma run in families. Some 30% to 60% of the world population is atopic and about two-thirds of these are asthmatics. Although mite allergens are carried in particles too large to penetrate the airways, there is evidence to suggest that domestic mites are the most common potential indoor allergen and a major cause of asthma world-wide. A correlation has been established between the level of mite density in a community and the observed occurrence of symptoms related to mite allergen exposure. Exposure to domestic mites in the first year of life also correlates with the subsequent development of asthma.

The term 'house dust mites' was used originally to refer to those mites belonging to the family Pyroglyphidae. At present, the term 'dust mites' is widely preferred and this refers to all pyroglyphid and non-pyroglyphidites that are implicated in dust borne respiratory allergy. At least 13 species of Pyroglyphidae have been recorded from house dust, of which six: *Dermatophagoides pteronyssinus, D. farinae, Hirstia domicola, Malayoglyphus intermedius* and *Euroglyphus maynei*, have been recorded repeatedly throughout the world. Of the four main groups of dust mites only those which are important in house dust will be considered here.

*Dermatophagoides pteronyssinus* (which literally means "skin-eating mites") is considered the 'true' house dust mite and is the dominant mite in constantly damp climates (Northern Europe, Brazil, and the Pacific Northwest). *D. farinae* survives better in drier climates than *D. pteronyssinus* and it is the most prominent mite species in areas with prolonged dry winters. Another domestic mite of importance is *Blomia tropicalis*, commonly found in houses in tropical and subtropical areas such as Brazil and Florida.

The allergens of domestic mites have been identified as cysteine proteases (group 1 allergens: *D. pteronyssinus* 1, *D. farinae* 1 and *D. microceras* 1); serine proteases (group 3 allergens), and amylase (group 4 allergens). These allergenic enzymes have been found in mite fecal pellets. The group 2 allergens are derived mainly from mite bodies rather than mite feces (*D. pteronyssinus* 2, D. farinae 2). The predominant allergens in house dust are from groups 1 and 3 and very little group 2 allergen has been found in dust. Group 4 mite allergens have only recently been described.

Together these species account for over 90% of the total mite population generally found in houses. As the species name implies, *D. farinae* (ex Latin farina=flour) also infests flour and stored food and is the subject of many recent and current studies. *Euroglyphus maynei* is studied relatively less than the Dermatophagoides because it is difficult to maintain in culture.

Mites are found at sites in houses which provide sources of food and shelter with adequate humidity. These include bed mattresses, carpets, upholstery and other textiles. The fibrous and cellular structure of these environments allows mites to cluster and reduce water loss. In general, more mites are found in bedrooms than any other rooms in homes (bed mattresses>furnishings>bedroom floors>lounge room floors) and, in fact, in the average double bed there are between ten thousand and two million house dust mites. Mite egg production is doubled in the presence of dried semen.

Carpeted floors harbor significantly more mites than tile or wood floors. There is also variability between types of carpets. Thus, short tight-piled carpets, such as those of the indoor-outdoor type also harbor significantly fewer mites than long, loose-pile carpet. Wood and tile floors also support only low populations of mites. Loose pile carpets apparently provide a microhabitat for accumulation of the food and moisture favorable for mite survival and breeding. They also offer protection against removal by vacuuming.

Seasonal distribution is also variable. Studies in the Wakayama area of Japan showed that house dust mites of the genus Dermatophagoides were more abundant in summer and autumn than in winter and spring. Fecundity appeared to be favored by high temperatures and a high relative humidity. In Semipalatinsk, Russia, autumn appeared to be the most favorable season for the reproduction of mites.

In Japan, larger numbers of mites were present in dust samples from concrete than wooden houses. This is attributed to the airtight construction of the former and high relative humidity created by tatami, a thick rectangular mat of woven straw commonly used on concrete floors. In Russia, however, mites are most numerous in old wooden and adobe-type structures with high humidity.

Mites are found in great numbers in basement and ground floor apartments. Generally, it seems that houses in lowlying areas and near coasts harbor more mites and, again, the probable reason is higher humidity levels encountered in such locations.

Mites feed on human and animal scales colonized by microfungi, yeasts, and bacteria. Their digestive system consists of a foregut, midgut and hindgut. In the foregut, which includes the mouth, pharynx and esophagus, ingestion and sucking of food particles take place. The midgut consists of a ventriculus and coecae where budding-off of cells from the walls promotes engulfment of food particles and promotes their breakdown during passage. Absorption then takes place through the gut epithelium into the hemolymph. The hindgut consists of a rectum and anus where there is dehydration and death of cells. Waste material is packaged into fecal pellets which are surrounded by a peritrophic membrane and then excreted.

The life cycle of Pyroglyphid dust mites consists of the egg, larva, protonymph, tritonymph and male and female adult stages. The duration of these stages depends on the species, available food and local habitat conditions. In general, optimum conditions for growth of house dust mites are temperatures of 20° C.–25° C. and relative humidity of 70%–80%. Further, life cycles overlap so that all the stages can be found at one season.

Mating may occur within 24 hours after emergence of adults, followed by production of eggs the rate of which varies between species. For example, a female *D. evansi* lays an average of 35.5 eggs while *D. pteronyssinus* lays 60–100 eggs during her lifetime. The total number of eggs laid per female is often referred to as fecundity. The rate of reproduction is the number of eggs laid per day during the reproductive period.

Mite control has, in the prior art, been an extremely difficult task. The current solution is to remove as much of the habitat of mites as possible and to make what remains inhospitable for them. Methods to reduce the number of mites have been developed mainly for affluent countries and little is known about the influence of different types of housing on mite populations in partly-affluent and non-affluent countries. However, the introduction of blankets into communities where they were not previously used has been shown to increase dramatically the number of mites in homes. A commercially available guanine assay kit (the Acarex™ test) may be used to assess house-dust mite levels in bedding, carpets and furniture fabric.

Physically encasing bedding and pillows is a quite effective mite control measure and is a commonly recommended approach. Permethrin impregnated nets have been trialled though their efficacy is not yet established. Regular weekly washing of fabrics at 55° C. or higher is effective in killing all mites. Unfortunately, high temperature washes are demanding for the less well off and can also damage fabrics. Washing in water alone is often, therefore, not completely successful. Some 10% of mites survive colder washes and can cause re-infestation. Dry cleaning kills all mites but it can be expensive to treat all items in a home and, additionally, may make life very difficult for residents whilst return of items is awaited. Ideally, carpets should be removed and replaced by vinyl or polished wooden floor boards. As will readily be appreciated, this is not a strategy which is easy for many families to implement, even in the affluent West. An alternative is to cover carpets with polyethylene sheeting, taped to the skirting board. This, too, is not popular since it indicates to all and any visitors that the household has an infestation problem.

Heat is quite effective in killing house dust mites. Superheated steam is an effective but drastic method sometimes used for treating carpets. Tumble-drying washing and exposure to strong sunlight have been claimed to be moderately successful control measures. Using electric blankets has also been claimed to reduce the number of mites on the grounds that the heat produced is a 'dry' heat, however, since using electric blankets often causes sweating, this raises humidity in the bed and lessens the overall effect. In extremely persistent or high density infestations, autoclaving of bedding is sometimes used but this is not a practicable routine approach.

Vacuum cleaning removes loose dust but has no effect on the number of live mites in the carpet since the mites are well adapted for attaching themselves to the fibers. Children's soft toys can be a potent source of domestic mite allergen and either should be removed, washed in hot water or deep frozen once a week. Vinyl, leather or plain wooden furniture is preferable to fabric covered furnishings though, again, few families can afford to scrap all their existing furniture. Ambient humidity can be reduced with dehumidifiers or air conditioning and maintaining the level below 50% is desirable.

Prior art acaricides, substances that kill mites via chemical action, include benzyl benzoate, (Acarosan™), pyrethroids, pirimiphos methyl, bromopol (Metsan™) and liquid nitrogen. These are used to some limited extent but their value is not proven at present. Both benzyl benzoate and tannic acid (a 3% solution denatures domestic mite allergen) are very effective in vitro, although the difficulty of applying them so that they reach deep into the pile or padding of furniture and carpets reduces their effectiveness. Other prior art acaricides include di-sodium octaborate tetrahydrate, finely divided common salt and oxazoline or thiazoline. The efficacy of these substances is influenced by a variety of factors within each home and by the delivery systems and these issues have not, as yet, been adequately addressed.

Long-term exposure to prior art acaricides requires rigorous safety and toxicity studies and they must be used regularly in order to achieve any worthwhile level of continuing control. Application of chemical acaricides to bedrooms, where children have prolonged contact with mattresses, pillows and carpets, is not generally recommended. Further, available data do not justify the use of fungicides in the control of domestic mites. Dead mites are more easily vacuumed up so thorough post-treatment vacuum cleaning is essential. Conventional insect sprays are of no benefit and may aggravate allergic symptoms.

The picture thus emerges of a number of potentially effective physical control measures for controlling dust mites, unfortunately none of which is generally practicable. In addition, there are a number of potentially effective prior art acaricides which are likely to prove toxic when used in confined spaces and on a regular basis—precisely the way they have to be used to provide any chance of effective control.

World wide, asthma is one of the most common chronic diseases, affecting up to 10% of the global population. The disease is on the increase and is also becoming more widespread, particularly among the young. The prevalence of asthma varies from almost 0% up to 30% in different populations.

In England alone, during the past two decades, there has been a rise of between three and five-fold in the number of children admitted to hospital for asthma, the figure varying between health regions. Childhood asthma is more prevalent in boys than girls. The predominant feature associated with asthma in children is allergy and it appears that domestic mites represent the major allergen causing asthma throughout the world, both in affluent and partly-affluent countries. The introduction of mites into the indoor environment through the use of blankets, such as has happened in Papua New Guinea or by the increasing use of insulation in houses, are probably important causes. Climate is of importance because it is directly related to the amount of allergen present in the environment. For example, a damp and warm climate is favorable to both mite and mould growth.

In the U.K., there are over 3 million people affected by asthma and it is the most frequent cause of absence from school through sickness. It is also amongst the most common reasons for repeated visits to GPs by children. The disease affects all age groups and is a chronic condition where the airways become obstructed to a varying extent and this prevents the sufferer from breathing properly. Asthma can impair the quality of life and is also a major cause of absence from work. Few data exist concerning the severity of asthma in major populations but Australian studies have shown that, although 8%–1% children and 6%–7% of adults have current asthma, about 4% of all age groups have moderate or severe asthma that requires regular medication. Asthma is a major public health issue with cumulative costs to individuals and countries. It deserves the attention of governments and public health systems since the implementation of effective treatment strategies for asthma is likely to reduce both morbidity and health care expenditures.

In the United States, for example, asthma in children accounted for 7.3 million days restricted to bed and 10.1 million days missed from school per annum. The impact is similar in England and Australia. In London, school loss because of wheezy illness was reported by 12% of children and amounted to more than 30 days missed per person for the academic year. In Australia, school loss caused by asthma accounted for approximately 965,000 days annually. The social burden goes beyond lost schooling: data suggest that 35% of children with asthma experience a great deal of pain or harassment as a result of their asthma, that 17% have symptoms often and that nearly 5% experience symptoms all the time. Children with asthma may be at higher risk of learning disability as compared with children without asthma. The impact of asthma on the children of any country, therefore, is likely to be both large and underestimated, at least in monetary terms. Data from developed countries clearly demonstrate this burden of asthma on children and suggest that it is even greater on a per-person basis in developing countries.

In adults, asthma symptoms lead to loss of work and decreased productivity, which can have substantial impact on the work force. For example, asthma is reported to account for more than 1.5 million days loss of production per year in New South Wales. Data from Britain have indicated 5.73 million days of certified incapacity for work in 1987–88 as a consequence of asthma. Similarly, asthma has contributed to nearly 1.9 million days of sick leave in Sweden annually. In addition, one study found that 25% of a sample of patients with asthma had experienced at least one period of four or more consecutive days off work, during a 6-month period, due to their asthma.

Asthma is greatly under-diagnosed and is often untreated, misdiagnosed or overlooked. When diagnosed properly it is treatable and the onset of asthma attacks can be dramatically reduced in frequency and severity if house dust mite populations are properly controlled. It occurs in all countries, regardless of the level of development, but appears to be more common in affluent than in non-affluent populations. The increase in prevalence of asthma is probably related to environmental factors, including increasing exposure to allergens such as house dust mites. Two thirds of all asthmatics are allergic to house dust mites.

Asthma is a not infrequent primary cause of death. Mortality data are of limited value because they are available for a relatively few countries and they are rarely available for different populations within the countries. Values since 1960 show that mortality rates in the U.S. and Canada are lower than in other countries, although there are wide variations in mortality rates within the U.S.

Asthma is also associated with atopy, a form of hypersensitivity to common, everyday particles (see above). Atopy and asthma are both familial and may be genetically based. Recent work has suggested that the gene may be on chromosome 11, coding for the beta-chain of the receptor that binds IgE to mast cells and, in some way, leads to an enhanced immune inflammatory response. Other groups believe that genes on chromosome 5 may be involved. Certainly, some chromosome 5 genes code for interleukins, which are substances linked to upregulation of IgE formation and growth and maturation of mast cells and eosinophils. These types of cells are heavily involved in the allergic, inflammatory response. In addition, there are other genetic factors relating to selective stimulation of the allergic response by agents in the environment.

As noted, asthma is a chronic inflammatory disorder of the airways. This inflammation causes recurrent episodes of symptoms, variable airflow limitation and increased airway responsiveness. The obstruction of the airways which occurs in asthma is called 'airway hyper-responsiveness'—airways that narrow too easily or too much in response to a provoking stimulus. In persistent asthma, the airways are hyper-responsive to many different provoking stimuli. Allergen exposure and chemical sensitisers are the most important risk factors for the onset of asthma. The most effective management is to prevent this inflammation by eliminating the causal factors since asthma can be effectively controlled in most patients, although it cannot be cured. The major factors contributing to asthma morbidity and mortality are under-diagnosis and inappropriate treatment.

The occurrence of asthma symptoms is closely related to the level of environmental allergens. Thus, indoor environmental control measures to reduce exposure to allergens are important, even though it is rarely possible to achieve complete control. Among the wide variety of allergens that occur within human dwellings, domestic mites are particularly important and their presence has been confirmed on a world-wide basis. Exposure to mite allergens in early childhood is known to be an important causal risk factor for development of asthma and the World Health Organisation has recognized domestic mite allergy as a universal health problem.

The Global Initiative For Asthma has stated that reducing exposure to domestic mites, especially for infants, appears to be a highly promising preventive measure because evidence suggests that domestic mite allergen is a major causal risk factor for asthma. As will now be apparent, physical measures directed towards mite control are rarely either practical or fully effective. Chemical control is also, at present, inadequate or potentially toxic.

Thus there is a significant need for a safe chemical method for dealing with domestic infestation with house dust mites which would address the issues which detract from the prior art products. An ideal product will offer freedom from toxicity and have a resistance-free mode of action.

The following US patents are considered relevant:

U.S. Pat. No. 4,666,940 U.S. Pat. No. 5,271,947 U.S. Pat. No. 5,578,625 U.S. Pat. No. 5,672,362

Other references considered relevant include:

Platts-Mills T A, et al. Dust mite allergens and asthma: report of a second international workshop. *J Allergy Clin Immunol* 1992; 89:1046–1060.

Platts-Mills T A E, de Weck A L. Dust mite allergens and asthma a worldwide problem. *J Allergy Clin Immunol* 1989; 83:416–427.

Platts-Mills T A, et al. Reduction of bronchial hyperreactivity during prolonged allergen avoidance. *Lancet* 1982; 2:675–678.

Platts-Mills T A E, et al. Role of allergens in asthma and airway hyperresponsiveness: relevance to immunotherapy and allergen avoidance, in Kaliner M A, Barnes P J, Persson C G A (eds), *Asthma: Its Pathology and Treatment*. New York, Marcel Dekker, 1991, ch 22.

Price J A, et al. Measurement of airborne mite antigen in homes of asthmatic children. *Lancet* 1990; 336:895–897.

Sporik R, Chapman M D, Platts-Mills T A. House-dust mite exposure as a cause of asthma. *Clin Exp Allergy* 1992; 22:897–906.

Sporik R, et al. Exposure to house-dust mite allergen (Der p 1) and the development of asthma in childhood. A prospective study. *N Engl J Med* 1990; 323:502–507.

OTHER MITES AND TICKS

The large group of Acarines, which includes ticks and chiggers as well as mites, is diverse and includes many parasites which are only attached to the host for relatively short periods. Many carry pathogens such as *Asian typhus* and, in addition, cause intense itching which can be partly due to the presence of the mites themselves and partly due to their secretions which can be allergenic. As well as causing disease in man, they infest birds, mammals and plants. Their infestation can be a cause of significant economic loss in animal husbandry and through serious damage to crops. Though small, mites are variable in size.

Of mites which live their entire lives attached to the host, there are two important groups. The Demodicidae are worm-like mites which live in the hair follicles of mammals, whereas the Psoroptidae and Sarcoptidae are mites which produce scab and mange.

The mite which produces human scabies is *Sarcoptes scabiei* and the condition was probably first described formally by Francesco Redi in 1687. *S scabiei* is round to oval, soft and is without eyes and has an anterior rostrum with chelae and four pairs of limbs. It is a burrowing mite which tunnels into the epidermal layer of the skin and its secretions cause severe irritation. The male is about half the size of the female, which is about 0.4–0.5 mm long. After mating the female deposits up to 25 eggs in the epidermal burrows, every two or three days, for about 2 months and then dies. The incubation period is usually 8–10 days but may range from 4 to 40 days or, occasionally, even more, after which the larvae repeat the life cycle in a similar manner and this leads to an ongoing infective process. It is for this reason that the condition is sometimes known as seven-year itch. Scabies is a highly contagious infestation characterized by intensely pruritic papular eruption.

Transmission between sufferers is usually by prolonged intimate contact but this may only involve hand-holding for a few minutes and may, occasionally, occur from contaminated objects such as bed sheets. Under some circumstances, *S scabiei* can survive outside the host for up to 2 days.

Symptoms, other than the intense itching, may be variable and depend, to some extent, upon duration of infection, the mite burden carried by the host, sensitization to parasite proteins and upon attempts at remedial action, particularly the general degree of hygiene. Mite burrows are narrow, whitish and almost always less than 1 cm long. Since scratching is so prevalent in the condition, the burrows are rarely observed intact and erythematous rashes with papules, nodules and vesicles are frequently seen at the infected sites. Very commonly, lesions are found on the wrists, hands, interdigital spaces, below the breasts and around the sexual organs but may occur anywhere. Diagnosis is usually clinical and confirmed by laboratory identification of the mite or eggs in skin biopsies or scrapings.

Lindane and permethrin lotions have been widely used for scabies and have been reviewed above. However, the longest established treatment is benzyl-benzoate baths or lotions. The latter is unpleasant to use and is a known skin irritant, especially on broken or erythematous skin which is precisely the skin condition encountered in established scabies, where much scratching will inevitably have taken place. Benzyl benzoate has also been widely used for treating mite infestations in animals.

ANTS

Many species and varieties of ants represent significant problems for man. Examples, non-exhaustively, include fire ants, brown ants, carpenter ants, pharaoh and flying ants. Foraging worker ants, having identified a food source, lay a chemical trail which will be followed by many co-worker and other ants, sometimes numbered in thousands. This level of infestation in domestic premises can be troublesome and even threatening, especially with varieties such as fire ants, the bite of which can be extremely painful.

SUMMARY OF THE PRESENT INVENTION

The present invention comprises pesticide formulations for killing terrestrial arthropods including, non-exhaustively, lice and lice eggs, mites, ants and other pests and which may optionally be presented, as a shampoo for use on the hair or other hairy body parts, a lotion and cream for use on the skin, a spray for the treatment of fabrics including infested bedding and upholstery, a dipping solution for the immersion of combs and an additive for use during washing of infested fabrics in a washing machine or other vessel. Formulations for use on infested animals include a drench and a dip. Preparations for killing terrestrial arthropods include aqueous and alcoholic liquids which may be, optionally, presented as sprays.

The shampoo for use in head and body lice infestation is user friendly compared to prior art products which require to be left on the hair for extended periods, referred to by those skilled in the art as 'dwell time'. To date the present authors have been unable to find any other dip based on any chemical formulation which is specifically intended for brushes and combs to provide a means for preventing re-infection by killing lice and lice eggs on such items.

The active ingredients which are employed in the instant invention include one or more terpenes, preferably those which are naturally occurring and generally unmodified. The preferred terpenes are classified as GRAS (Generally Regarded as Safe) by the Environmental Protection Agency in the U.S.A. and have been used for many years in the flavor and fragrance industries.

Certain of the preferred individual terpenes employed in the instant invention are highly effective against both lice and lice eggs and it is considered extremely unlikely that resistance can develop, due to their observed modes of action. Unlike the active principles of most other pediculocides, the terpenes used in the instant invention are not neurotoxins.

The terpenes may be used in conjunction with citral, a terpene aldehyde, which is derived from certain essential oils, in particular lemongrass (*Cymbopogon citratus*). Although citral is known to have limited antibacterial and anti-fungal effects and lemongrass oil has been used as an insect repellent, we have not found previous reports indicating that citral is an effective pediculicide or miticide.

The instant invention provides optimized blends of a terpene concentrate and citral which we have shown to be powerful and synergistic in their cidal action against infesting arthropods.

The shampoo formulation is mild, has a pH which may be slightly basic to neutral and has a pleasant odor. It also preferably contains one or more conditioning agents so that no separate conditioning is necessary. Overall, the product is safe and pleasant to use and is generally acceptable for children, the major end-users for a treatment for head lice. The lotion formulation, used, by way of example, but non-exclusively, as a scabicide, employs the active ingredients in similar proportions. The lotion and spray formulations are highly effective against the house dust mite *D. Pteronyssimus*. Comb dip and spray products may also be based on the shampoo formulation using a lower concentration of the active ingredients. A laundry additive product may also be based on the shampoo formulation with the addition of a surfactant preferably, though not necessarily, a non-ionic surfactant.

Electron microscopy studies have shown that the principal mode of action against adults and larvae is by direct solvent action on the epicuticle, removing wax which is essential for preventing water loss and desiccation.

DETAILED DESCRIPTION OF THE PRESENT INVENTION

The present invention is a series of arthropodicidal, particularly pediculicidal, and miticidal pesticide formulations containing one or more terpenes together with the terpene aldehyde citral. Optimally the terpenes include:

| |
|---|
| Redistilled limonene; |
| Beta-ionone; |
| Linalool; |
| Geraniol; |
| Eugenol; and |
| either Myrcene or Carvone. |

The rationale for the individual constituents and their use in combination is as follows:

Limonene is used in the present invention series as an adjuvant to enhance the properties of other terpenes. The redistilled version is strongly preferred because it has a low-odor compared with natural d-limonene which has a very strong citrus smell and soon oxidizes, producing an unpleasant aldehyde odor. Redistilled limonene is also more stable than natural d-limonene.

Beta-ionone is an effective pediculicide which also has significant anti-bacterial and anti-fungal properties. In head lice infestation, especially in children, lice feeding sites on the scalp often become secondarily infected as a result of scratching and the problem of scratching is even worse with mite infestations, such as scabies. The anti-bacterial and anti-fungal properties of beta-ionone reduce the chances of secondary infection occurring and, when applied frequently to an already infected area, represent a moderately effective treatment strategy. Body lice as well as many mites and other insect parasites are known to be positive primary vectors for bacteria or fungi, however, the anti-bacterial and anti-fungal properties of beta-ionone have some prophylactic value in respect of this risk.

Linalool and Geraniol are both effective pediculocides which have similar properties and similar levels of activity to beta-ionone, with which they are synergistic.

Geraniol is also incorporated because of its pediculicidal, anti-bacterial and anti-fungal actions and is mutually synergistic with both beta-ionone and linalool. In addition, geraniol adds a definite and pleasant fragrance.

Eugenol is the active terpene in clove oil. It has topical anaesthetic properties which are valuable in controlling the itching associated with mites and with lice and their feeding sites. Eugenol also acts in further synergistic cooperation with beta-ionone, linalool and geraniol in respect of pediculicidal, anti-bacterial and anti-fungal actions. Eugenol also imparts a further distinct fragrance which is pleasantly compatible with that of geraniol.

Myrcene is added mainly for its fragrance properties, however, it does have limited pediculicidal, anti-bacterial and anti-fungal actions. Carvone is found to be a suitable substitute for Myrcene and has different fragrance properties, so as to give the product a different aroma.

In preferred embodiments, a mixture of five of the terpenes named above is blended together briefly—the constituents are readily mutually miscible.

Advantageously, the terpene blend is then further blended with citral.

A sufficient volume of the resultant blend is then added to a good quality base according to the purpose required. For instance, in respect of a pediculicidal shampoo, a good quality, conditioning shampoo base may be used, to produce an optimal concentration of the active ingredients in the blended mixture as shortly hereinafter described for preferred embodiments. The final concentration of the active ingredient ranges from 0.5% to 20% by weight of the active ingredient in the final volume of the pesticide. More preferably, when the terpene aldehyde citral is added as an additional active ingredient, the final concentration of the active ingredient ranges from 0.5% to 20% by weight, 2.0% to 10% by weight, or 1.75% to 7% by weight of the active ingredient in the final volume of the pesticide.

Maximal pediculicidal, miticidal and general pesticidal activity is obtained when the resultant product has an initial pH adjusted to between 8 and 8.5, though the exact value between these limits is not critical.

The slightly basic shampoo provides the surfactant mechanism needed to enable the terpenes/citral combination to kill lice at a low level of concentration under conditions of normal use. Terpenes are non-polar and have no affinity for the exoskeleton of lice. The surfactant effect allows generalized contact of the terpenes with the exoskeleton. Experiments have shown that survivability of lice, mites and other terrestrial arthropods is irreversibly compromised after a brief exposure. The same mechanism may be observed in larvae and with egg cases but sometimes takes longer and may require an additional application. Experiments have also led to preliminary observations which suggest that the instant invention softens the adhesive which lice employ to secure eggs to a human hair shaft.

When it is required to use a terpene formulation, according to the present invention, as a washing additive, the use of a specific additional surfactant is necessary. We have found that non-ionic, anionic and cationic surfactants all produce satisfactory results but that non-ionic surfactants are markedly superior.

ORIGINAL EMBODIMENT

The active ingredients of a formulation for killing lice and eggs which infest humans are blended in the following percentages by volume given with respect to an active ingredient of the insecticide:

| | |
|---|---|
| Redistilled limonene | 45% |
| Beta-ionone | 25% |
| Linalool | 10% |
| Geraniol | 10% |
| Eugenol | 5% |
| Myrcene | 5% |

We preferred, in this embodiment, to use a concentration of 4% by volume of this terpene blend in an aqueous shampoo, containing ammonium lauryl sulfate and ammonium laureth sulfate as a base, with palmitic acid or glycol distearate and other minor ingredients as conditioning agents. This concentration was preferred because, at this level, there is a pleasing gelling effect with the shampoo base, the resulting product was highly pediculicidal and, in experiments, there was no evidence of adverse effects on human users. Higher concentrations of the terpene blend are unnecessary and might lead to problems of minor irritation in a small proportion of the population. Later, It was found that carvone could be substituted for myrcene, and achieve better fragrance properties.

Experiments have shown that the formulation, diluted with distilled water to a 2% terpene blend concentration is also pediculicidal. The 2% concentration product may advantageously be used as a spray to kill lice and their eggs on fabrics, including bedding, upholstery and clothing. This product is useful against body lice which, unlike head lice, can survive and live comfortably off a human host and infest fabrics between blood meals.

The 4% formulation, hereinbefore described, may be diluted with distilled water to a 1% terpene blend concentration. This approaches the lowest practicable level and requires significantly increased exposure (dwell time). This would detract from the use of this concentration as a shampoo, since long dwell times are known to be a barrier against user compliance with prior art shampoos used against lice. However, the 1% concentration may be applied advantageously and in a novel manner as dip solution for the immersion of combs between uses by multiple family members and those in institutionalized groups to prevent cross infection and re-infection. Obviously, immersion times will vary but will generally be extended and sufficient to achieve effectiveness.

The terpene blend of the instant invention may be used in concentrations from about 20% up to 50% by volume as an additive for washing Infested fabrics. In this application, the product requires the addition of a surfactant which is optimally the non-ionic surfactant polysorbate 80 at an overall concentration of up to 10%. The product may be used in either a hot wash (typically 60° C.) or a cold wash (ambient water temperatures). Washing may optionally be carried out in a machine and the process may be an active (agitated) or a passive (steeping) wash.

EXAMPLES

Method of Preparation—Terpene Concentrate

In a round bottom flask equipped with a stirring bar are placed redistilled limonene (45.0 g) beta-ionone (25.0 g), linalool (10.0 g), geraniol (10.0 g), eugenol (5.0 g), and myrcene (5.0 g). The resulting mixture is stirred at room temperature for two minutes. The flask is then stoppered and the blend stored until required.

In another round bottom flask equipped with a stirring bar is placed 96 g of a conditioning shampoo containing ammonium lauryl sulfate and ammonium laureth sulfate as a base with palmitic acid or glycol distearate and other minor ingredients as conditioning agents.

To the second flask is added 4 g of the terpene blend and the contents are stirred slowly at room temperature for about three minutes until gelling is observed to be complete. The resultant product is then decanted into a screw top container and stored at room temperature until required.

The product is used in the manner of an ordinary conditioning shampoo which is to say that the hair is wetted, the shampoo is applied thoroughly all over the hair and scalp and then left in place for one to two minutes, after which it is rinsed off with plenty of warm water.

A spray for the treatment of infested bedding and upholstery is prepared by diluting the shampoo product with distilled water to a concentration of 2% in a suitable flask.

A comb dip is prepared by diluting the shampoo product with distilled water to a concentration of 1% in a suitable flask. The resultant product is stored in a wide mouth, screw top container until required. Additives for use during washing of lice infested fabrics in a washing machine or other vessel are prepared by adding the terpene blend to distilled water to produce a final concentration of 20% to 50% by volume. Sufficient of the non-ionic surfactant polysorbate 80 is added to produce an overall concentration of 10%.

Use as a Pediculicidal Agent—Initial Group Of Experiments

Experiment 1: Approximately 5 g of fresh hair croppings from an individual heavily infested with head lice (Pediculosus humanus capitus), were placed on a large glass slide and promptly examined under a low power light microscope to confirm the presence of at least ten live lice and ten eggs. Within five minutes of the microscopic examination, the slide and hair croppings were transferred to a shallow glass vessel. Approximately 15 ml of distilled water at about 45° C. was added to the hair croppings which were stirred with a glass rod until the hair was wetted thoroughly. Excess water was then decanted from the vessel and set aside in a small flask. About 2 ml of a shampoo preparation containing 4% of the terpene blend, prepared as described under 'Method of Preparation' above, was added to the wet hair croppings which were turned repeatedly with a glass rod for about 30 seconds to ensure distribution of the shampoo throughout the whole sample, which was then tamped gently for a further 30 seconds to simulate a light scalp massage. At the end of this procedure, the hair croppings were transferred to a very fine mesh sieve and subjected to two rinses each in separate one liter flasks containing 500 ml of distilled water at about 45° C.

The hair sample was then transferred on to white filter paper and microscopically examined for lice and eggs. Both rinses were filtered and the filter papers microscopically examined for lice and eggs.

No live lice were found. All eggs were non-viable and showed alterations to the casing and reduction in size of the adhesive band attaching them to the hair shaft. A considerable number of eggs were found which were not attached to hair shafts.

Experiment 2: The observation of detachment of eggs from hair shafts, seen in Experiment 1, may have occurred due to mechanical manipulation, however, in a parallel experiment, where plain water was used but all other conditions were similar, very few eggs became detached from hair shafts suggesting that action of the active Ingredients in the shampoo had been responsible for the detachments observed in Experiment 1 where the shampoo was used.

Experiment 3: A commercially available steel 'nit comb' was used to comb the hair of the heavily infested individual who provided the hair croppings for Experiment 1, at about the same time the hair sample was taken. The comb was placed on a large glass slide and examined with a suitable low power light microscope and the presence of significant numbers of eggs and a few live lice disposed on and between the teeth of the comb was established.

The comb was placed in a wide mouth vessel containing 250 ml of a comb dip prepared as described under 'Method of Preparation' above and left for 30 minutes. At the end of this period the comb was removed gently and allowed to drain over the vessel. It was then placed on a filter paper and examined microscopically. The contents of the wide mouth vessel were then filtered, together with two washings each of 100 ml of tepid distilled water. The filter paper was then examined microscopically. Only dead lice were found together with non-viable eggs.

The product is used at a 1% concentration level as a comb dip to prevent cross infection and re-infection between family members and institutionalized groups.

Experiment 4: A shirt taken from an individual moderately infested with body lice was microscopically examined. A considerable number of live lice and eggs were observed. The shirt was carefully placed in a large polythene bin and sprayed, using a simple plunger mist-spray device filled with a spray liquid prepared as described under 'Method of Preparation' above and left for 30 minutes. About 40 ml were used. At the end of the period, the shirt was once again subjected to careful microscopic examination. Only dead lice and non-viable eggs were found.

Experiment 5: Several items of clothing, including a shirt, trousers and underwear were taken from an individual moderately infested with body lice and microscopically examined. Live lice and eggs were observed in most but not all the items. The clothes were placed carefully in a large polythene bin of 5 gallons capacity containing water at ambient temperature (19° C.), to which 50 ml of a wash additive of 40% concentration, prepared as described under 'Method of Preparation' above had been previously added and stirred in. The aim was to achieve a concentration of the terpene combination in the washing water of at least 0.25%. The clothes were pushed under the surface gently with a polythene rod and left for one hour. At the end of the period, the shirt was removed from the bin, compressed gently to remove most of the water and then once again subjected to careful microscopic examination. Only dead lice and non-viable eggs were found.

Experiment 6: Several items of clothing, including a shirt, trousers and underwear were taken from an individual moderately infested with body lice and microscopically examined. Live lice and eggs were observed in most but not all the items. The clothes were placed carefully in a washing machine to which 50 ml of a wash additive of 20% concentration, prepared as described under 'Method of Preparation' above had been previously added. The aim was to achieve a concentration of the terpene combination in the washing water of at least 0.25%. In addition, the normal manufacturers specified amount of domestic detergent was added, appropriate to the cycle and load. The washing machine was set to a standard agitating wash cycle involving rinse and spin stages and having a maximum temperature of 50° C. and a duration of 41 minutes. At the end of the cycle, the clothes were once again subjected to careful microscopic examination. No lice and only a few non-viable eggs were found.

In a control experiment using a similar batch of clothes washed in the same machine on the same cycle but without the laundry additive of the instant invention, no live lice were found but some eggs were found after the wash cycle still adhering to seams. A small number of these were thought possibly to be viable.

The method of preparation and experiments in the uses of the instant invention are quoted by way of example only and it will be evident to those skilled in the art that single terpenes and other combinations of terpenes employing some or all the terpenes described as well as other methods of preparation, concentrations and numerous other uses may be derived without departing from the scope and spirit of the invention.

Discussion On Initial Experiments

The initial group of experiments produced encouraging results with the original embodiment of the instant invention. However, in retrospect, we were concerned that in some respects, the approach we had taken may not have been sufficiently challenging or rigorous. For instance, in experiments 1 through 3, we have since considered that, in true user situations, a larger amount of water might be admixed with the terpene shampoo and that this might negatively affect performance. We also believed it was important to try to investigate the mode of action of the active terpene mixture and any effects it might have on human hair. Furthermore, in respect of the performance of the shampoo, we were interested to investigate how development of the shampoo base might affect performance of the active ingredients. We also had concerns over the well known fact that head lice do not survive readily off a human host and typically die within about ten hours and it was, therefore, decided to consider surrogate arthropod species for testing purposes. Finally, we did not feel that either we or prior workers in the art have adopted a sufficiently rigorous approach to determining kill rate and thus decided to continue any future observations for 24 hours to preclude or monitor any recovery of treated arthropods.

Accordingly, we designed a series of experiments to deal with these and other issues and derived a further embodiment hereinafter described.

Experiment 7: This was, essentially, a repeat of Experiment 1, but using 20 ml of washing water in order to achieve an 'ultimate dilution' of 1:10. The kill rate was reduced and there was no kill with a water control experiment.

Experiment 8: This experiment involved the method of Experiments 1 and 7 but using the shampoo base only, in 20 mls of washing water In order to achieve an 'ultimate dilution' of 1:10. There was an apparent kill rate of about 40% with extended contact and there was no kill with a water control experiment.

MOST PREFERRED EMBODIMENT—PESTICIDAL SHAMPOO

A shampoo base was prepared with a view to optimizing the characteristics required to promote contact of a terpene mixture with infesting arthropods. The following ingredients are mixed in a suitable vessel:

| | |
|---|---|
| Primary surfactant | 14.95% w/w |
| Secondary surfactant | 1.08% w/w |
| Foam stabilizer/thickener | 2.70% w/w |
| Thickening agent | 1.92% w/w |
| Pearlizing agent | 2.00% w/w |
| Conditioning agent | 0.60% w/w |
| Chelating agent/softening agent | 0.40% w/w |
| Active ingredients and water | to 100% |
| Triethanolamine: sufficient to adjust the pH to 8.0 | |

Conveniently, the primary surfactant may be sodium lauryl ether sulfate, the secondary surfactant may be sodium lauryl sulfate, the foam stabilizer may be coconut diethanolamide, the conditioning agent may be pantothenol, the thickening agent may be cocamideopropyl betaine, the pearlizing agent may be 20% sodium alkyl ether sulfate and 17% ethylene glycol monstearate and the cleating agent may be EDTA. These and the other agents may be obtained commercially from Surfachem Ltd, Leeds, LS1 4DP, U.K. and BDH, Poole, Dorset, BH15 1TD, U.K. We now believe that using sodium lauryl ether sulfate and sodium lauryl sulfate is preferable to using ammonium lauryl sulfate and ammonium laureth sulfate, since the latter two compounds, when used at the optimal levels of pH, are close to the point at which they may release ammonia. Advantageously, the formulation is stabilized with a small quantity of sodium chloride.

Water used in the preparations and in the experiments hereinafter described was produced by reverse osmosis, nuclear de-ionization and filtration and nominally complies with the requirements of the PhEUR and USP specifications for Purified Water.

The batch water is warmed to 45° C. and stirred whilst adding the chelating agent, secondary surfactant and primary surfactant, foam stabilizer, thickening agent and conditioning agent. The mix is then allowed to cool whilst mixing and the pearlizing agent and active ingredients (terpene mix and citral) are added. The batch volume is adjusted with water and the resultant mixture is stirred thoroughly. Finally pH is adjusted with triethanolamine Citral was investigated for its potential as a pesticidal component and because of its potential as a skin conditioning agent in situations where scratching has taken place. Citral was obtained from New Seasons, Wantage, Oxfordshire U.K.

Brown ants were selected for the initial test species since they are readily available and robust.

General Method for Testing Pesticidal Properties of Shampoo Formulations

Under standardized laboratory conditions of 18° C.–20° C., normal atmospheric pressure (1 bar±0.05 bar) and away from direct sunlight, brown ants were exposed to 1:10 (by volume) dilutions of the formulations and thereafter observed under controlled conditions. 10 ants were placed in a small glass vial and the test solution applied. Ants were exposed using a combination of shaking and a rotary mixing. Subject ants were then washed using 3×100 ml aliquots of water and a Buchner vacuum funnel was set up containing a Whatman Number 50 filter paper. The filter paper and ants were then removed and placed in a Petri dish. A quantity of sugar was placed on a vial-top as food. The Petri dish was labeled and sealed with tape to prevent dehydration. Sequential, timed observations were then made.

In some cases, inconsistent results were obtained at 0.5 hours and 1 hour after exposure. It was established that apparent death rates at these early intervals were due to the washing procedure, rendering the ants inactive during this early period of observation.

Validation Of The Drying Process Used In This Series

Tests were conducted to validate the experimental control procedure. It was considered possible that the Buchner funnel vacuum process involved in the drying procedure might damage ants.

In a first Water Control Group, 10 ants were immersed for 30 seconds in 10 mls water and then carefully dried with a Buchner apparatus and treated in accordance with the standard procedure.

In a second Water Control Group, 11 ants were immersed for 30 seconds in 10 ml water and then carefully retrieved manually, placed on a Whatman No. 50 filter paper and thereafter treated in accordance with the standard procedure. The results for both groups are summarized in Table 1.

TABLE 1

| | Time after exposure (hours)/Apparent death rate (%) | | | | | | |
|---|---|---|---|---|---|---|---|
| Test solution | 0 | 0.5 | 1 | 2 | 4 | 5 | 24 |
| Water Control 1 | 40 | 40 | 20 | 10 | 10 | 20 | 10 |
| Water Control 2 | 27 | 0 | 9 | 0 | 9 | — | 9 |

From Table 1, it may be seen that there was little difference in survival rate between the drying methods, thus a Buchner apparatus was used for drying the ants since this procedure was easier to standardize and control.

Shampoo Formulations Evaluated

Table 2 lists the shampoo formulations tested in accordance with the standard method.

TABLE 2

| Test Shampoo | Terpene Mixture | Citral | Standardized shampoo base |
|---|---|---|---|
| 4% Terpene shampoo (Carvone 5%) | 4 parts (5% Carvone) | nil | 96 parts |
| 4% Terpene shampoo (Myrcene 5% | 4 parts (5% Myrcene) | nil | 96 parts |
| Shampoo base with Citral 3% | nil | 3 parts | 97 parts |
| Shampoo base with Citral 5% | nil | 3 parts | 97 parts |
| 4% Terpene shampoo (Carvone 5%) with Citral 5% | 4 parts (5% Carvone) | 5 parts | 91 parts |
| 4% Terpene shampoo (Carvone 5%) with Citral 10% | 4 parts (5% Carvone) | 10 parts | 86 parts |

TABLE 2-continued

| Test Shampoo | Terpene Mixture | Citral | Standardized shampoo base |
|---|---|---|---|
| 2% Terpene shampoo (Carvone 5%) with Citral 5% | 2 parts (5% Carvone) | 5 parts | 93 parts |
| 2% Terpene shampoo (Carvone 5%) with Citral 2% | 2 parts (5% Carvone) | 2 parts | 96 parts |
| 3% Terpene shampoo (Carvone 5%) with Citral 3% | 3 parts (5% Carvone) | 3 parts | 94 parts |
| 4% Terpene shampoo (Carvone 5%) with Citral 2.5% | 4 parts (5% Carvone) | 2.5 parts | 93.5 parts |

It is to be clearly understood that the terpene mixtures, used in the shampoos evaluated, contain carvone or myrcene as 5% of the total terpene mix but that the strength of the shampoo, in respect of terpenes, is stated with respect to total terpenes. For the sake of clarity, the carvone or myrcene expressed as a percentage of the total terpene mix (but not of the shampoo) is stated in parentheses. Where citral was used in the shampoos evaluated the percentages stated are with respect to the shampoo and are independent of and separate from the terpene mix.

Experiments to Evaluate Terpene Mixtures Containing Carvone Against An Otherwise Substantially Similar Mixture Using Myrcene Table 3 shows the results of exposing ants to shampoos containing 4% of a terpene mixture with 1: Carvone (5%) and 2: Myrcene (5%) for 2 minutes. Shampoo base and water control experiments were also conducted.

TABLE 3

| Test solution | Time after exposure (hours)/Apparent death rate (%) | | | | | | | |
|---|---|---|---|---|---|---|---|---|
| 2 Minutes exposure | 1 | 2 | 3.25 | 4 | 8 | 19 | 20.5 | 24 |
| 4% Terpene shampoo (Carvone 5%) | 10 | 10 | 10 | 10 | 10 | 90 | 100 | 100 |
| 4% Terpene shampoo (Myrcene 5%) | 30 | 0 | 10 | 10 | 10 | 80 | 90 | 90 |
| Shampoo base | 10 | 10 | 10 | 10 | 10 | 40 | 40 | 40 |
| Water control | 0 | 0 | 0 | 0 | 0 | 20 | 30 | 30 |

From Table 3, it may be seen that shampoo containing the 4% terpene mixture including carvone, and that including myrcene, were both effective in killing all ants within 24 hours. Carvone appeared marginally more effective though this is of marginal statistical significance.

Experiments To Evaluate Pesticidal Properties Of Citral

This series was conducted to determine the pesticidal activity of citral using a one-minute exposure time. The general method was employed, however, in addition, ants were exposed to a moist filter paper containing one drop of citral (neat and not incorporated into shampoo base) and placed in a Petri dish for observation. A control experiment for this test involved the use of a moist filter paper with no test substance added.

Table 4 shows the results of exposing ants to shampoos containing 1: Citral (3%) 2:Citral (5%) and 3: The results of exposing ants to one drop of citral on a moist filter paper. In this series it is important to note that the exposure time was 1 minute. A shampoo base control experiment was conducted and a water control was carried out for the single drop citral experiment. It is also important to note that the terpene mixture was not included in these shampoos.

It will be appreciated that, under conditions of practical use, in humans and animals, an exposure of one minute probably represents the practical lower limit period for which any shampoo preparation could realistically be deployed and removed.

TABLE 4

| Test Solution 1 | Time after exposure (hours)/Apparent Death Rate (%) | | | | |
|---|---|---|---|---|---|
| Minute exposure | 0.5 | 1 | 2 | 4 | 24 |
| Shampoo base with Citral 3% | 100 | 100 | 100 | 80 | 70 |
| Shampoo base with Citral 5% | 60 | 50 | 50 | 20 | 10 |
| Shampoo Base | 50 | 50 | 10 | 0 | 0 |
| Moist filter paper + 1 drop Citral | 40 | 100 | 90 | 100 | 100 |
| Water Control (Moist filter paper) | 0 | 0 | 10 | 10 | 20 |

From Table 4, it may be seen that shampoo formulations containing citral, at both 3% and 5% levels, demonstrated a clear pesticidal effect in the ant model. Neither formulation achieved a 100% kill rate in 24 hours but, counter-intuitively, citral at the 3% level had a significantly greater effect than citral at the 5% level. The shampoo base control experiment indicated that this had no lasting effect when used with a very short exposure time.

The study with the moist filter paper containing citral shows an apparent death rate of 100% after 24 hours. This clearly demonstrates the pesticidal effect of citral under the test conditions.

Apart from its pesticidal properties, demonstrated here, citral is known to have a hypersensitivity quenching property with respect to limonene and although limonene, in dilute aqueous solutions, is not a common sensitizer it is advantageous good practice to include means for limiting and reducing adverse reactions in any formulation intended for use on human skin, particularly that of children.

Experiments To Evaluate The Effect Of Adding Citral To The Terpene Mixture

The terpene mix including carvone was selected for this series of tests, mainly because it has a preferable fragrance.

Table 5, shows the results of exposing ants to shampoos containing 4% of a terpene mixture with 1: Carvone (5%)

and citral forming 5% of the total shampoo; 2: Carvone (5%) with citral forming 10% of the total shampoo. The exposure time in both cases was 2 minutes. Shampoo base and water control experiments were also conducted.

From Table 6, it may be clearly seen that shampoo formulations containing 4% of the terpene mixture and those containing 2% of the terpene mixture (both with carvone included at the 5% level) demonstrated a significant

TABLE 5

| Test solution | Time after exposure (hours)/Apparent death rate (%) | | | | | | | |
|---|---|---|---|---|---|---|---|---|
| 2 minutes exposure | 1 | 2 | 3 | 4 | 5 | 6 | 8 | 24 |
| 4% Terpene shampoo (Carvone 5%) with Citral 5% | 0 | 10 | 10 | 20 | 20 | 20 | 30 | 100 |
| 4% Terpene shampoo (Carvone 5%) with Citral 10% | 10 | 20 | 20 | 20 | 20 | 30 | 30 | 100 |
| Shampoo Base | 0 | 0 | 10 | 10 | 10 | 10 | 20 | 30 |
| Water Control | 0 | 0 | 0 | 0 | 10 | 10 | 10 | 40 |

From Table 5, it may be seen that ants exposed to a shampoo containing the 4% terpene mixture (including 5% carvone), with the addition of 5% citral, demonstrated a 20% higher apparent death rate at 8 hours following a 2 minute exposure when compared to the effect of the same shampoo without citral—see Table 3.

Experiments To Evaluate Terpenes With Citral Shampoo Formulations

This series was conducted to determine the most effective terpene plus citral shampoo formulation. Table 6, shows the results of exposing ants to shampoos containing the terpene mixture as follows: 1: 4% terpene mixture (carvone 5%); 2: 4% terpene mixture (carvone 5%) with citral forming 5% of the total shampoo; 3:2% terpene mixture (carvone 5%) with citral forming 5% of the total shampoo; 4:2% terpene mixture (carvone 5%) with citral forming 2% of the total shampoo. In this series it is most important to note that the exposure time was reduced to 30 seconds. Shampoo base controls but not water control experiments were also conducted. It will be appreciated that, under practical use conditions, in humans and animals, such preparations could not realistically be deployed and removed in such a short period.

improvement in the apparent death rate of ants when citral was present and forming 5% of the shampoo formulation. In fact, the performance of the formulations with citral as 5% of the shampoo were remarkable, given the brevity of exposure.

The results also indicate that formulations containing 2% of the terpene mixture, with citral forming 2% and 5% of the shampoo, were not very effective when used with a very short exposure time. This indicates that the limits of effectiveness, at least in respect of exposure time, have been exceeded.

Experiments To Evaluate A Further Terpenes With Citral Shampoo Formulation

This challenging series was designed to investigate the effect of an additional variation in the proportions of the active ingredients in order to further investigate kill rate, following an exposure of only 30 seconds. Table 7 shows the results of exposing ants to shampoos containing the terpene-mixture as follows: 1:–3% terpene mixture (carvone 5%) with citral forming 3% of the total shampoo; 2:4% terpene mixture (carvone 5%) with citral forming 2.5% of the total shampoo; 3:4% terpene mixture (carvone 5%) with citral forming 5% of the total shampoo. In this series it is most important to note that the exposure time was less than the lowest practical time limit for deploying and removing the shampoo under normal conditions.

TABLE 6

| Test solution | Time after exposure (hours)/Apparent death rate (%) | | | | | | |
|---|---|---|---|---|---|---|---|
| 30 second exposure | 0 | 0.5 | 1 | 2 | 4 | 5 | 24 |
| 4% Terpene shampoo (Carvone 5%) | 100 | 70 | 60 | 30 | 50 | 50 | 0 |
| 4% Terpene shampoo (Carvone 5%) with Citral 5% | 100 | 60 | 80 | 100 | 100 | 100 | 100 |
| 2% Terpene shampoo (Carvone 5%) with Citral 5% | 100 | 100 | 90 | 90 | 100 | 90 | 90 |
| 2% Terpene shampoo (Carvone 5%) with Citral 2% | 100 | 40 | 30 | 30 | 0 | 0 | 0 |
| Shampoo base | 100 | 20 | 10 | 0 | 0 | 0 | 0 |

TABLE 7

| Test Solution | Time after exposure (hours)/ Apparent death rate (%) | | | | |
|---|---|---|---|---|---|
| 30 second exposure | 0.5 | 1 | 2 | 4 | 23 |
| 3% Terpene shampoo (Carvone 5%) with Citral 3% | 90 | 90 | 90 | 70 | 70 |
| 4% Terpene shampoo (Carvone 5%) with Citral 2.5% | 100 | 90 | 30 | 20 | 10 |
| 4% Terpene shampoo (Carvone 5%) with Citral 5% | 90 | 100 | 100 | 90 | 90 |

From Table 7, it may be seen that, in this series, the formulation containing 4% of the terpene mixture (including carvone 5%) with citral forming 5% of the total shampoo fell somewhat short of achieving maximal kill rate in 23 hours (note that in the previous experiment on this formulation the final observation was made at 24 hours). It is also clear that the formulation containing 3% of the terpene mixture (including carvone 5%) with citral forming 3% of the total shampoo, produced an encouraging kill rate at 23 hours, considering the very short exposure time and, when compared to the lower kill rate achieved with the shampoo containing 2% of the terpene mix (including carvone 5%) with citral 2%, of the previous series—see Table 6.

It was noted that the formulation containing 3% of the terpene mixture (including carvone 5%), with citral forming 3% of the total shampoo, had a more pleasing scent than that of the stronger formulation containing 4% of the terpene mixture (including carvone 5%) with citral forming 5% of the total shampoo. This formulation may be used, suitably diluted, as a drench for arthropod infested farm and domestic animals, however, a specific drench formulation is hereinafter described.

Experiments To Compare The Effectiveness Of Terpenes With Citral Shampoo Formulations Against Three Commercially Available Shampoo Preparations This series of experiments was designed to evaluate the performance of the instant invention against three leading commercial products, using the ant model. The formulations of the instant invention selected contained: 1:4% of the terpene mixture (including carvone 5%) with citral forming 5% of the total shampoo and 2:3% of the terpene mixture (including carvone 5%) with citral forming 3% of the total shampoo.

The exposure time selected was 2 minutes. The grounds for selecting this exposure period were that, since the formulation is a conditioning shampoo, in normal use it should not need to be left on the hair any longer than the time associated with a normal thorough conditioning shampoo procedure in the home. We have previously timed a number of individuals instructed to wash their hair thoroughly with a conditioning shampoo and found a mean of a little under 90 seconds, start to finish. However, when observing parents washing the hair of children known to have head lice, they invariably shampoo for longer, with a mean of about 2 minutes 15 seconds.

In the case of the commercially available preparations, the manufacturers' instructions concerning the period of exposure were followed exactly. All the commercial preparations were within their 'use by' dates at the time of the experiments. These preparations, together with the method of exposure, were as follows:

Lyclear Crime Rinse™, Warner Lambert, Eastleigh, SO53 3ZQ, U.K., (1% Permethrin with Propyl Parahydroxybenzoate as preservative), Lot. A7A2494: Diluted 1:10 in water. Ants were exposed to the diluted solution in a Petri dish for 10 minutes and were thereafter rinsed with water.

Suleo-M Lotion™, Seton Scholl Healthcare (formerly Seton Healthcare Group), Oldham, OL1 3HS, U.K., (0.5% Malathion in an alcoholic base), Lot. 8L 398:1 ml of the neat preparation was decanted onto a filter paper. Ants were exposed to the preparation for 2 hours and were thereafter rinsed with water.

Full Marks Liquid™, Seton Scholl Healthcare (formerly Seton Healthcare Group), Oldham, OL1 3HS, U.K., (0.5% Phenothrin with Propyl Parahydroxybenzoate as preservative), Lot. 9B 282: 1ml of the neat preparation was decanted onto a filter paper. Ants were exposed to the preparation for 16 hours and were thereafter rinsed with water.

TABLE 8

| Test solution | Time after exposure (hours)/ Apparent death rate (%) | | | | |
|---|---|---|---|---|---|
| 2 Minutes exposure | 0.5 | 1 | 2 | 4 | 24 |
| 4% Terpene shampoo (Carvone 5%) with Citral 5% | 100 | 100 | 100 | 100 | 100 |
| 3% Terpene shampoo (Carvone 5%) with Citral 3% | 100 | 100 | 100 | 100 | 100 |
| Test solution Exposure varies | | | | | |
| Lyclear Creme Rinse ™ (10 minutes) | 100 | 100 | 100 | 100 | 100 |
| Suleo- M Lotion ™ (16 hours) | 100 | 100 | 100 | 100 | 100 |
| Full Marks Liquid ™ (2 hours) | 50 | 100 | 100 | 100 | 100 |
| Water Control | 100 | 90 | 90 | 10 | 10 |

From Table 8, it may be seen that all the preparations tested achieved a 100% apparent kill rate at the one hour observation and no recoveries were seen in any ant group at any time. However. it should be noted that the manufacturers' recommended periods of contact were completed before observations began, thus, one of the commercially available preparations was in contact with the subject ants for 16 hours, one for 2 hours and one for 10 minutes, prior to the first observation period. These contact periods are in marked contradistinction to that employed with the instant invention.

It will also be noted that the formulation containing 3% of the terpene mixture (including carvone 3%) with citral forming 3% of the total shampoo, was no less effective with a 2 minute exposure, than the formulation containing 4% of the terpene mix with citral forming 5% of the total shampoo. However, the formulation of the shampoo base containing less active ingredients was noted to have a pleasant 'lemony' scent, somewhat less marked than with the formulation containing 4% of the terpene mixture and 5% citral.

Experiments To Evaluate A Terpenes With Citral Shampoo Formulation In The Treatment Of Body Lice Human body lice from a culture colony maintained at a specialist medical entomology center were used in tests, under the terms of a confidentiality agreement, to study the effects of a shampoo, according to the present invention, and containing a 3% terpene mixture (carvone 5%) with citral forming 3% of the total shampoo. This center is experienced in carrying out trials of pediculicides.

Adult females and males, in approximately equal numbers, were used for each test. The lice were fed on the morning of the test and allowed a minimum of 4 hours to recover, during which time they were able to excrete excess water imbibed with their blood meal. Lice were counted into batches of 20 insects, each of which was provided with a square of an open meshed nylon gauze (tulle), as a substrate upon which to stand. Each batch was allocated to a marked 30 mm diameter plastic Petri dish. Each test group of lice consisted of three replicate batches of 20 lice.

The shampoo was used diluted in a similar manner to a conventional toiletry shampoo, at the rate of one part shampoo plus nine parts water (1:10). As hereinbefore indicated, this dilution was based on the principle that a head of reasonably short hair holds approximately 80–100 ml of water, when wetted prior to shampooing and, in areas where the water contains moderate quantities of calcium and other minerals, most people would use approximately 8–10 ml of shampoo on hair of this type.

Approximately 5–10 ml of the diluted shampoo was poured into the base of each clean 30 mm diameter plastic Petri dish. Each gauze bearing the lice was immersed in the fluid for 2 minutes, during which time the gauze was turned twice to ensure removal of air bubbles.

After removal from the fluid, the gauze and insects were rinsed three times, using 250 ml of warm tap water at 34° C. poured through and over the gauze squares. The squares were then lightly blotted to remove excess fluid and returned to their marked Petri dishes. The same procedure was repeated for the other replicate gauze squares in that batch.

Each batch of lice were tested in comparison with a control group exposed to water only and. A water control experiment was also done. All other handling procedures for the controls were identical to those applied to the test insects.

The gauze squares bearing adult lice were incubated under normal maintenance conditions (30±2° Celsius and 50%±15% relative humidity) for 24 hours, at which time the results were recorded.

The kill rate with diluted shampoo, according to the present invention and containing a 3% terpene mixture (carvone 5%) with citral forming 3% of the total shampoo, of about 50% was high in comparison with earlier trials with permethrin and carbaryl where lower kill rates were observed at 24 hours. Furthermore, the test population was selected to contain only adults, whereas a normal population would contain 20% to 30% juveniles, which are considerably more susceptible to pediculicides. The true effectiveness was thus probably somewhat understated. These studies are ongoing.

Dosage implications

Anthropometric data suggests that the human scalp has an area between 500 sq. cm and 750 sq. cm. and further that the heads of the majority of young children may reach the $80^{th}$ percentile by the $5^{th}$ year. On this basis, the scalp of a 5 year old child treated with a shampoo formulation, according to the instant invention and containing 3% of the terpene mixture (including carvone 5%) with citral forming 3% of the total shampoo, would receive 120 µg cm.

We know of no reports of serious adverse reactions with the terpenes or citral used topically in the instant invention and the only reports of any adverse reactions we have found relate to minor skin reactions. Indeed, as discussed hereinbefore, the use of citral with limonene is likely to reduce any such incidence and the virtual absence of toxicity is in marked contradistinction to prior art products which include neurotoxins and carcinogens. The extremely low toxicity profile of the instant invention represents a major benefit and advance in the art of treating arthropod infestation of humans and animals.

We have thus used the shampoo delivered dosage of 120 µsq. cm. as the baseline for developing further formulations intended for the treatment of arthropod infestations, modifying this where the nature of the treatment demands, or where there are opportunities for extended exposure of the organism, or where circumstances allow rational and economical exposure to larger amounts of the active ingredients of the formulation.

Atomic Force Microscopy Investigation Of Effects Of The Instant Shampoo Formulations On Human Hair In a further attempt to establish the safety of the shampoo formulations we arranged for independent Atomic Force Microscopy (AFM) studies to be conducted on human hair treated with shampoo formulations according to the present invention. The studies were conducted under the terms of a confidentiality agreement. It has previously been shown that this technique can be a useful tool for demonstrating subtle changes in hair exposed to different liquids in real time.

An East Coast Scientific AFM equipped with 16 µm tube scanner was employed using a $Si_3N_4$ microlever with a nominal spring constant, k=0.03 N/m. The AFM was operated in the force versus distance mode (Fd), whereby the approaching/retracting tip senses interaction at the interface with the surface. Tip displacement is measured using a laser and a position sensitive photo-diode detector Each test was conducted on a separate hair fiber mounted in specially prepared metal slugs in such a manner that it was partially contained and so remained rigid during the test. Each slug was mounted in a liquid cell and oriented so that the AFM probe was perpendicular to the long axis, thus facilitating access to the hair. The test liquid was introduced subsequently into the cell.

Time resolved Fd spectra were obtained in aqueous environments to compare the state of the surface of the hair and to compare mechanical properties before and after treatments. The reference point was hair in de-ionized water. The hair samples, in all cases, were from a 6-year old human female. The scope of the tests is shown in Table 9.

TABLE 9

| Test solution | Exposure - minutes | Number of tests |
|---|---|---|
| De-ionised water | 60 | 7 |
| Shampoo base | 0–40 | 12 |
| Shampoo base diluted 100:1 | 0–40 | 10 |
| 4% Terpene shampoo (Myrcene 5%) diluted 100:1 | 0–50 | 12 |
| 4% Terpene shampoo (Carvone 5%) diluted 100:1 | 0–120 | 10 |
| 4% Terpene shampoo (Carvone 5%) diluted 10:1 | 0–30 | 13 |
| 4% Terpene shampoo (Myrcene 5%) diluted 10:1 | 0–30 | 11 |

The surface of the hair was softer after treatment with both shampoo base alone and with terpene containing shampoos (including both myrcene and carvone), when compared to treatment with water alone. A compliant layer was identified after treatments with both the shampoo base and the terpene containing shampoos. This compliant layer was thickest following treatment with a terpene containing shampoo (including carvone 5%) when diluted 100:1 with de-ionized water.

The effect of the terpene shampoo is most likely to remove the surface lipid layer allowing water to penetrate the outer layer of the hair fiber causing "softening" and swelling of the fiber as the fiber absorbs water. As the fiber swells it goes into radial compressive stress, becoming more rigid.

Although treatment with a terpene containing shampoo (including carvone 5%) at a dilution of 1:100 had the greatest effect, after prolonged exposure (2 hours) of the hair to this formulation, the soft layer of the hair was no longer detectable.

Shorter duration lower dilution tests mimic, to some extent, the situation where an over-zealous parent or adult user, might leave the terpene containing shampoo of the instant invention in contact with the hair for considerably longer than the recommended period of 2 minutes under otherwise 'normal use' conditions. Tests with terpene containing shampoos (including carvone 5%) diluted 1:10 and conducted for periods between 5 and 15 minutes indicated a compliant layer range of thickness between about 50 and 100 nm, which was intermediate between the values for de-ionized water and diluted shampoo base.

Longer duration higher dilution tests mimic, to some extent, the situation where a user does not thoroughly rinse the hair after using the shampoo.

Although further work is ongoing to Investigate further and to confirm the trends observed, the general similarity between the results obtained with shampoo formulations according to the instant invention containing terpenes and shampoo base alone, using varying exposure periods and dilutions, seem to indicate that it is unlikely that the instant invention exerts any significant deleterious effects on human hair.

Electron Microscopy Investigations

Light microscopic examination of dead lice and lice eggs, subjected to exposure to the terpene containing shampoos used in the experiments of the series relating to both embodiments, indicated barely visible alterations to the exterior of the adult lice but significant changes to the ligand, or adhesive band, between nits and hair shafts with loss of mass of the latter. We, therefore, undertook a detailed study of treated and untreated lice and lice eggs using scanning electron microscopy (SEM) and transmission electron microscopy (TEM).

Materials and methods

Head lice and lice eggs were harvested from human subjects. Lice and lice eggs were prepared for electron microscopy, as hereinafter described, without being subjected to any treatment with the instant invention. Lice and lice eggs were also treated with the terpene and terpene with citral containing shampoos of the Instant invention, all shampoo formulations being diluted in 10 volumes of water. Treated lice and lice eggs were also prepared for electron microscopy as hereinafter described. It is to be noted that in both groups, care was taken to select a number of specimens of lice eggs attached to human hair shafts.

All SEM and TEM specimens were subjected to primary fixation with half strength Kamovsky reagent (2 hours at room temperature) rinsed 4 times (10 minutes each rinse) in cacodylate buffer and then subjected to secondary fixation with Osmium tetroxide (1 hour at room temperature). This was followed by 4 rinses (10 minutes each rinse) in reverse osmosis water After rinsing, specimens for TEM examination were block stained overnight at 295° K. with 0.5% aqueous uranyl acetate and rinsed again.

Both TEM and SEM specimens were then dehydrated slowly, in six stages, each of 30 minutes, using a range of ethanol solutions. SEM specimens were dehydrated in 100% dry ethanol for an additional period before being critical-point dried.

TEM samples were serially infiltrated with Spurr resin and embedded in resin moulds prior to sectioning. Polymerization was undertaken in an oven for 10 hours at 343° K. Specimens, which included whole lice and lice eggs, sections of same and sections of lice eggs attached, with their ligand, to human hair shafts, were examined. The equipment used was:

1. A Hitachi S800 Field Emission Scanning Electron Microscope using various voltages according to the specimen type. This equipment is capable of producing Magnifications in the range ×200 to ×20,000.
2. A JEOL 1200EX Transmission Electron Microscope, again at various voltages according to specimen type. This equipment can produce magnifications in the range ×200 to ×75,000.

Discussion and Results

The arthropod exoskeleton or cuticle of arthropods, which is secreted by the underlying epidermis (sometimes called the hypodermis), is chitinous and comprises a thick (up to 200 $\mu$m) inner layer called the procuticle and an outer layer, called the epicuticle. The epicuticle is known to play a major role in reducing water loss and preventing death by desiccation, especially in terrestrial arthropods, including, non-exhaustively, lice, mites and ants, where it also acts as a water repellent. The epicuticle is rich in lipids—mainly waxes—and this is quantitatively added to and replaced by additional wax secretion produced by sub-cuticular glands and exuded via pore canals. It is, however, very thin (0.03–4.0 $\mu$m). The water repellent action of the waxy epicuticle is known to be the major reason why terrestrial arthropods do not drown in drops of rainwater. Furthermore, some experts in this field believe that the development of the waxy epicuticle, providing protection against desiccation, is the first amongst the five most important reasons for the evolutionary success of terrestrial arthropods in general and insects in particular.

We found from SEM photomicrographs that, at moderate magnification, the epicuticular surface of a normal, untreated, head louse Is rather uneven, having a somewhat 'dirty' appearance. This is in marked contradistinction to the condition seen in SEM photomicrographs of a head louse, treated according to the present invention, where the epicuticle has been denuded, leaving a pristine surface.

We took comparative TEM photomicrographs of sections through the integument in the abdominal region of prepared, adult head lice both untreated and killed by treatment according to the present invention. We found that, in treated samples, the epicuticle was much thinner and had been substantially removed.

Our electron microscopy findings with treated lice and lice eggs support our experimental observations in the ant model. They also support our results with various terrestrial arthropods and with wax-coated glass slides and the view that formulations of the terpene mixture, and formulations of the terpene mixture with citral, as active ingredients, according to the instant invention, when presented in an appropriate base which promotes contact with the epicuticle of arthropods, exert an effective solvent action upon the epicuticular lipid content causing rapid death by desiccation and/or causing drowning.

Electron photo-microscopy studies of the effects of the instant invention on the ultrastructure of various arthropods are ongoing.

Reference:

In Ruppert and Barnes "*Invertebrate Zoology*", 6$^{th}$ Ed, inter alia p600 & p 826; Saunders College Publishing Experiments on the Chitinous Integument of Crustacea Although there is no reasonable doubt that formulations, according to the instant invention, have been shown to kill infesting terrestrial arthropods by irreversibly damaging the waxy epicuticle, we considered that there may be an additional mode of action, albeit, considerably less important, and that this may involve the digestion of chitin, which is a major component of the arthropod exoskeleton.

Aquatic arthropods have a much less significant epicuticle than terrestrial arthropods and this is not surprising, given that their natural environment is not one where desiccation is likely. In addition, it is known that the integument of crabs allows passage of gases and water and this is particularly the case with structures such as the gill covers. The chitinous content of the crustacean exoskeleton is thus substantially exposed to and, accordingly, we acquired fragments of crab chitin, from a commercial source, in order to study the effects of exposing it to formulations according to the instant invention.

In a series of chitin exposure experiments which included painting, soaking and spraying samples with formulations containing terpene mixtures with and without citral at various concentrations and dilutions there was, in almost all cases, a noticeable effect. Most commonly this comprised a change in texture from 'firm' or 'friable' to 'spongy' or 'soft'. Because the sample material was extremely variable in thickness and general character, it was difficult to reach more definite conclusions from physical examination or even by inspecting unbroken or fractured surfaces under the light microscope.

Subsequently, sections of untreated and treated crab chitin from the same sample fragment have been compared by TEM. It was observed that, with respect to the cut surface of the untreated portion of the sample, the ultrastructure of the exoskeleton is somewhat dense, apparently perforate and rather consistent across the field. In respect of the cut surface of the treated portion, it was observed that areas of the structure had been excavated and a number of the 'perforations' had become linked, rendering the ultrastructure less dense. It is not possible to say with certainty at this stage whether the porous material of structure was actually chitin but this seems at least likely. What may be said, with a reasonable degree of confidence, is that exposure of crab exoskeleton to formulations according to the present invention, under various conditions, leads to a degree of loss of mass with concomitant (and in life probably irreversible) structural damage.

We believe that, in circumstances where the instant formulations are used against terrestrial arthropods at moderate concentrations and with extended exposure times, it is probable that the epicuticle is removed first and that the procuticle is then attacked, most likely by limited solvent action on chitin. In most small terrestrial arthropods, it seems unlikely that any direct action on chitin would be of any significance before death supervenes as a consequence of epicuticular de-lipidization. However, the secondary action on the procuticular structure may be a further valuable factor in long term avoidance of the development of resistance as well as being of potential value in larger infesting arthropods with a relatively massive exoskeleton.

Experiments To Confirm The Direct Solvent Action On Waxes Of The Instant Invention In Aqueous Solution:

In order to confirm that an aqueous solution, according to the present invention, dissolves insect-derived waxes, we obtained pure beeswax from a commercial source for the following experiments.

Ground glass microscope slides were carefully wiped clean and weighed. The slides were each then thinly coated, on one side, with beeswax by warming them and pouring the molten wax over one surface. The wax was then allowed to cool and set.

Each slide was then weighed again and then immersed in the test solution for 2 minutes without stirring or agitation. Each slide was then rinsed in purified water and dried at 40° C. for 20 minutes, then allowed to cool. Each slide was then subjected to a final weighing.

Table 10, shows the results obtained using this procedure with diluted and undiluted shampoo, both according to the present invention and both containing a 3% terpene mixture (carvone 5%) with citral forming 3% of the total shampoo. A water control experiment was also carried out.

TABLE 10

| Test Solution<br>2 minutes exposure | Total<br>Weight of<br>Beeswax | Percentage of<br>beeswax<br>remaining<br>following<br>exposure |
|---|---|---|
| Purified Water (control) | 0.1704 g | 100% |
|  | 0.1904 g | 100% |
| 3% Terpene shampoo (Carvone 5%) with Citral 3%, | 0.2148 g | 98.92% |
| 1 part shampoo diluted with 9 parts Water | 0.2528 g | 99.28%<br>mean 99.10% |
| 3% Terpene shampoo (Carvone 5%) with Citral 3%, | 0.2381 g | 94.49% |
| Undiluted | 0.2278 g | 97.36%<br>mean 95.92% |

The results in Table 10, show clearly that an aqueous solution, according to the instant invention, does have a direct solvent action upon insect derived waxes. The undiluted shampoo concentrate removed considerably more beeswax from the slide than did the dilute solution. However, it is important to note that even the shampoo concentrate contains only 6 parts in 100 of active ingredients. The dilute solution was also effective in removing wax from the slide in the 2 minute experiments and in this case only 6 parts of active ingredients are present in 994 parts of water.

If considered superficially, the amounts of wax removed by the shampoo, according to the instant invention, may appear to be small in comparison to the total amounts of wax coating the microscope slides. However, such a conclusion would only be reached by one who had failed to appreciate the very small amounts of wax involved in forming the extremely thin epicuticular covering in terrestrial arthropods. Viewed in that context, the de-waxing capability of the instant invention, as demonstrated, is devastating.

Formulation Of An Additive For The Washing Of Laundry Containing Terpenes With Citral A phosphate free washing additive base for use during the washing of laundry infested with terrestrial arthropods may be prepared by mixing the following in a suitable vessel:

| Primary surfactant (anionic) | 16.00% w/w |
|---|---|
| Secondary surfactant with optical brightener | 10.00% w/w |
| pH regulator | 6.00% w/w |
| Thickening agent and stabilizer | 3.00% w/w |
| Builder | 1.00% w/w |

| -continued | |
|---|---|
| Silicone based antifoam agent | 0.15% w/w |
| Purified water (reverse osmosis water) | 46.85% w/w |
| The active ingredients comprise:- | |
| Terpene mixture (including carvone 5%) | 10.00% w/w |
| Citral | 7.00% w/w |

Conveniently, the primary surfactant may be a commercial product, Calflon CC55™ (55% solution), the secondary surfactant with optical brightener may be another commercial product, Calflon DP 1110™ (30% solution), the pH regulator may be sodium carbonate, the thickening agent and stabilizer may be sodium chloride, the builder may be sodium metasilicate and the silicone based antifoam agent may be a further commercial product, FAC 10™. The commercial products may be obtained commercially from Ellis & Everard, Middlesborough, Cleveland, TS3 8BD, U.K.

The primary surfactant is dissolved in a quantity of cold water and the secondary surfactant is added, with mixing, which is continued for 20 minutes. Then, during further mixing, are added the builder, pH regulator, silicone based antifoam agent and thickening agent and stabilizer. Mixing is continued for 15 minutes. With further mixing, the terpene mixture (including 5% carvone) is then added, followed by the citral. Mixing is continued for a further 20 minutes.

The additive may be used with infested clothing, children's soft toys and bedding which may be contaminated with terrestrial arthropods such as lice or mites.

200 ml of the washing additive is added either directly to the wash load, using a suitable dispenser, or to the main detergent dispensing cache, according to preference, in a domestic washing machine. The wash volume of a typical modern automatic washing machine is about 3.5 liters to 5 liters, depending upon the wash cycle selected. The dilution of the concentrate washing additive will thus be from 1:17 to 1:25. The 'delivered amounts' of active ingredients in the wash water will thus be about 7 mg per ml to about 9 mg per ml.

In cases of heavy infestation, 150 ml of the formulation may be used as a pre wash in which the laundry items may be left to soak for any desired prolonged period before commencing the main wash cycle with the additive as immediately hereinbefore described. The pre-wash volume of a typical modern automatic washing machine is about 3 liters. The dilution of the concentrate washing additive, in this case, will thus be 1:20. The 'delivered amount' of ingredients in the pre-wash water will thus be about 8 mg per ml.

Formulation of an Aqueous Lotion Containing Terpene Mixture With Citral

A lotion formulation, according to the present invention, was made using a lotion base prepared by blending the following:

| Base | 14.00% w/w |
|---|---|
| Base | 5.75% w/w |
| Emollient | 7.75% w/w |
| Surfactant | 2.40% w/w |

| -continued | |
|---|---|
| Antimicrobial preservative | 0.95% w/w |
| Purified water (reverse osmosis water) | 64.90% w/w |
| The active ingredients comprise:- | |
| Terpene mixture (including carvone 5%) | 2.50% |
| Citral | 1.75% |

Conveniently the base Ingredients may be white soft paraffin and liquid paraffin, the emollient may be cetostearyl alcohol, the surfactant may be sodium lauryl sulfate and the antimicrobial preservative may be phenoxyethanol, all of which are readily available commercially.

The active ingredients are blended into the base to produce a white to slightly off-white lotion with a fresh and pleasant lemon odor. This lotion has excellent spreading characteristics and is absorbed into human skin with minimal rubbing action. It also has good moisturizing properties. All items used in the lotion base have British Pharmacopoeia raw material specifications.

The lotion is intended to be applied and left in situ until the occasion of the next bath or a subsequent application. Since sarcoptic mites burrow, it was necessary to assume that they would not necessarily be immediately exposed to the active ingredients and, therefore, application would be repeated, normally once or twice during each day. It was also considered valid to employ a higher 'delivered amount' of active ingredients with each application than was employed with the shampoo formulations.

In order to determine an application rate, three adult human males had the area of their dorsal, lateral and medial forearms measured and marked. The mean area was 620 sq. cm. Three plastic bottles were each weighed accurately. A quantity of the lotion was then introduced into each bottle which was then weighed again in order to accurately determine the weight of the lotion in each bottle. Each subject was given one bottle of lotion and instructed to apply it to the first measured forearm area. The subjects were requested that the amount of lotion used be such as to spread onto and into the skin of the test area so that no white lotion remained visible, only a slight sheen on the skin. The subjects were instructed not to use vigorous rubbing to achieve this. The lotion bottles were then weighed again and the amount used by each subject was calculated by difference and recorded. This procedure was then repeated on the second forearm, in the same manner, and the amount used calculated. The mean usage in the six experiments was 2.2 g which equates to a 'delivered amount' of 150 $\mu$g sq. cm. and this reflects the specific requirement to achieve adequate contact with sarcoptic mites encountered in scabies.

Cream and Gel Formulations Containing Terpene Mixture with Citral

By using the ingredients of the lotion and increasing the quantities of white soft paraffin and cetostearyl alcohol, a stiff white cream base may be formed. A gel base may be formed by the addition of carbomer (carboxypolymethylene) or xantham gum. We contemplate that all and any of these bases may be appropriate to the presentation of the instant invention in the treatment of mites and other infestations by terrestrial arthropods.

Treatment of Mites Using a Lotion According to the Present Invention

A major purpose of the lotion is as a scabicide preparation and it was decided to conduct preparatory work to demonstrate the general miticidal effectiveness of the formulation, using substitute or analogue species. This was first undertaken using the red spider mite and a spray formulation and these experiments are hereinafter described.

Thereafter, experiments were carried out using the house dust mite, *Dermatophagoides pteronyssinus*. Since this species is, as hereinbefore stated, a major target species in its own right, the experimental work served a dual purpose, although it should be carefully noted that the house dust mite does not live on man and does not burrow in the manner of *Sarcoptes scabiei*.

Healthy cultures of *Dermatophagoides pteronyssinus* were obtained, commercially, from the Royal Agricultural College, Cirencester, Gloucestershire, U.K. (Dr Barbara Hart) and maintained in environmental cabinets at 25° C. and a relative humidity of 70%.

Three fresh pig cadaver skin samples, each having an area of approximately 20 sq. cm, were prepared by cutting and then conditioning by washing under tepid running water then placing in an oven at 40° C. for 10 minutes to dry. Thereafter each skin sample was placed in a small Petri dish.

50 mgm of lotion was then loaded onto each of 2 skin samples and lightly rubbed into the skin using a surgically gloved finger until the lotion was completely dispersed and only visible as a slight sheen on the skin surface. 5 mg of a live culture of *Dermatophagoides pteronyssinus* was spread gently and evenly over the center of each of the duplicate skin samples. A glass lid was placed over each Petri dish, which was then placed in an incubator at 25° C. and 70% relative humidity. It was previously determined by serial experiments that 5 mgm of the live culture contained approximately 250 live mites. The third pig skin sample was used for a water control experiment prepared simultaneously by the application of 50 mgm of water onto the skin surface.

The application rate, calculated from the amount of lotion applied and the area of the pig skin samples, equates to 106 μgm sq. cm. of active ingredients per sq. cm overall.

TABLE 11

| Test solution | Number of live mites at 30 minutes | Number of live mites at 60 minutes |
|---|---|---|
| Water control | 250 | 250 |
| Lotion formulation | 0 | 0 |

From Table 11, it may be seen that the lotion formulation, according to the instant invention, is highly effective against the house dust mite *Dermatophagoides pteronyssinus* under the experimental conditions employed.

Carpet Shampoo Formulation Containing Terpene Mixture With Citral

This formulation, which in a number of respects is similar to that developed as an additive for the washing of laundry, may be used on carpets, curtains, upholstery and bedding mattresses infested by terrestrial arthropods, particularly house dust mites and may be prepared by mixing the following in a suitable vessel:

| | |
|---|---|
| Primary surfactant (anionic) | 16.00% w/w |
| Secondary surfactant with optical brightener | 10.00% w/w |
| pH regulator | 6.00% w/w |
| Thickening agent and stabilizer | 1.50% w/w |
| Builder | 1.00% w/w |

-continued

| | |
|---|---|
| Silicone based antifoam agent | 2.50% w/w |
| Purified water (reverse osmosis water) | 53.00% w/w |
| The active ingredients comprise:- | |
| Terpene mixture (including carvone 5%) | 5.00% w/w |
| Citral | 5.00% w/w |

Conveniently, the primary surfactant may be a commercial product, Calflon™ CC55 (55% solution), the secondary surfactant with optical brightener may be another commercial product, Calflon™ DP 1110 (30% solution), the pH regulator may be sodium carbonate, the thickening agent and stabilizer may be sodium chloride, the builder may be sodium metasilicate and the silicone based antifoam agent may be a further commercial product, FAC 10™. The commercial products may be obtained from Ellis & Everard, Middlesborough, Cleveland, TS3 8BD, U.K.

The primary surfactant is dissolved in a quantity of cold water and the secondary surfactant is added, with mixing, which is continued for 20 minutes. Then, during further mixing, are added the builder, pH regulator, silicone based antifoam agent and thickening agent and stabilizer. Mixing is continued for 15 minutes. With further mixing, the terpene mixture (including 5% carvone) is then added, followed by the citral. Mixing is continued for a further 20 minutes.

The rate of use of the carpet shampoo depends upon the machine type and items to be treated. The intended method of application is with domestic or industrial applicators having an unheated reservoir. In a domestic machine with a tank reservoir volume of 2.5 to 3 liters, 300 ml of the concentrate is decanted onto the empty tank which is then topped up with water and agitated for a few seconds to achieve dispersion. The intended dilution is thus between 1:8.33 and 1:10. The 'delivered amounts' of active ingredients in the carpet shampoo, as applied, will thus be about 9 mgm per ml to about 11 mg per ml.

Drench or Dip Formulation Containing Terpene Mixture with Citral for Use on Animals This formulation is a concentrate for use in the eradication of terrestrial arthropod infestations In domestic and farm animals, including mite and tick infestations, and may be prepared by mixing the following in a suitable vessel:

| | |
|---|---|
| Surfactant (non-ionic) | 30.00% w/w |
| pH regulator | 6.00% w/w |
| Stabilizer | 3.00% w/w |
| Purified water (reverse osmosis water) | 51.00% w/w |
| The active ingredients comprise:- | |
| Terpene mixture (including carvone 5%) | 5.00% w/w |
| Citral | 5.00% w/w |

Conveniently, the non-ionic surfactant may be polysorbate 80, the pH regulator may be sodium carbonate and stabilizer may be sodium chloride, all obtained commercially.

The non-ionic surfactant is dissolved in a quantity of cold water, with mixing, which is continued for 10 minutes. Then, during further mixing, are added the pH regulator and stabilizer. Mixing is continued for 15 minutes. With further mixing, the terpene mixture (including 5% carvone) is then added, followed by the citral. Mixing is continued for a further 20 minutes.

The concentrate is diluted 1:10 with water in a suitable immersion tank and agitated to ensure dispersion prior to use. This formulation may also be used to spray crops infested with terrestrial arthropods such as, non exclusively, mites. The 'delivered amounts' of active ingredients in the drench, dip or crop spray, as used, will thus be about 7 mgm per ml to about 10 mg per ml.

Aqueous Spray Formulation Containing Terpene Mixture With Citral

An aqueous spray formulation, according to the present invention, was made using a base prepared by mixing the following:

| | |
|---|---|
| Surfactant (non-ionic) | 10.00% w/w |
| Solubilizer | 10.00% w/w |
| Purified water (reverse osmosis water) | 70.00% w/w |
| The active ingredients comprise:- | |
| Terpene mixture (including carvone 5%) | 5.00% |
| Citral | 5.00% |

Conveniently, the non-ionic surfactant may be polysorbate 80 and the solubilizer may be Solulan 98™, both obtained commercially.

The active ingredients are mixed into the base to produce a white opaque spray solution with a fresh and pleasant lemony odor.

The spray is intended to be used on areas infested by arthropods and left in situ until a subsequent application, should this prove necessary. Host targets include animals such as dogs and cattle suffering from infestation, as well as free-ranging troublesome domestic insects such as flies, mosquitoes and ants.

Since application to human skin is not contemplated for this formulation it is possible to employ a higher 'delivered amount' of active ingredients with each application than was employed with the shampoo formulations.

In order to determine a nominal application rate, a plastic pump spray bottle containing a quantity of the instant spray formulation was weighed accurately on a calibrated balance. A conical flask was used for collecting the output from a two second spray burst from the plastic pump spray. The plastic pump spray bottle was then re-weighed. This procedure was repeated twice more and the mean weight of spray delivered was 0.8 gm. The notional spray area was determined by firing the spray, from a distance of 30 cm, at an absorbent surface and measuring the diameter of the circle of wetness. This area was determined as 284 sq. cm. Using the delivered amount from a 2 second spray and the notional spray area, it may be calculated that the 'delivered amount' of active ingredients is about 282 μg per sq. cm.

Experiments on Various Terrestrial Arthropods With an Aqueous Spray Formulation Containing Terpenes With Citral In these experiments, various terrestrial arthropods were subjected to a single spray of about 2 seconds, using the spray formulation of the instant invention hereinbefore described containing a 5% terpene mixture (carvone 5%) with citral forming 5% of the total spray. The spray employed was a pump spray producing a fine mist and was directed at insects from a distance of not less than 20 cm and not more than 30 cm.

Table 12 shows the results of exposing various insects to the 5% terpene mixture (carvone 5%) with citral forming 5% of the total spray. No water control experiment was carried out.

TABLE 12

| Insect | Knock down | Death |
|---|---|---|
| Wasps | <1 minute | <4 minutes |
| Bluebottles | Instantaneous to 1 minute | <5 minutes |
| House flies | <45 seconds | <2 minutes |
| Flying queen ants | <15 seconds | <2 minutes |
| Brown ants | Immobilized <10 seconds | <2 minutes |
| Mosquitoes | Instantaneous to 1 second | <10 seconds |
| Red spider mite | Instantaneous | Instantaneous |
| Crickets | <30 seconds | <1 minute |
| Locusts | <1.5 minutes | <5 minutes |
| Wood louse | Immobilized <10 seconds | <3 minutes |
| Harvestman | Instantaneous | Instantaneous |
| Bees | Minimal effect | Behaved normally in <4 minutes |

The result with red spider mites was particularly interesting as these experiments were precursors to other work on mites. Red spider mites, which belong to a group of serious agricultural pests, died instantly, even when struck by only a partial spray. In contrast, several species of bees were used in experiments and the effects were minimal. This may be due to the dense hairy surface of the integument.

Experiments on House Dust Mites With an Aqueous Spray Formulation Containing Terpenes With Citral Early light microscope observations on samples from live, healthy cultures of Dermatophagoides pteronyssimus, the house dust mite, placed on a suitable substrate in a Petri dish, indicated that, when warmed about 10° C., or more, above their normal incubation temperature of 25° C., many mites migrated rapidly to and up the side walls. These observations provided the basis for the following experiments.

New hessian backed carpet with pile of 5 mm length and of wool and nylon construction was placed in an oven for 4 hours at 60° C. to kill any resident mites. Using a template, the carpet was then cut into disks of 9 cm diameter, area 63.6 sq. cm, and inoculated with 0.25 gm of a thriving dust mite colony containing about 12,500 individuals.

One carpet disk was subjected to a 2 second spray of a spray formulation, according to the instant invention, containing a 5% terpene mixture (carvone 5%) with citral forming 5% of the total spray, from a distance of about 30 cms. The other disk was subjected to a 2 second spray of purified water from the same distance. Each carpet disk was then placed in a duran basin, covered with a watch glass cover and left for three hours at room temperature, out of direct light.

In order to maintain humidity, 0.5 ml purified water was then placed in the bottom of each basin, on the opposite side from the carpet. Both basins were then heated to approximately 50° C. on a hotplate (fuzzy logic controlled) for 15 minutes, with the watch glass removed after 10 minutes.

After removal from the heat source, observations under a light microscope showed activity in the water treated sample, where mites, which had migrated to the top of the carpet pile, were moving rapidly back into the pile, as the sample cooled. In the sample treated with the spray, according to the instant invention, only dead mites were observed.

The basins were then covered again and left for a further 21 hours, at room temperature. Observations using the above technique were conducted and again numerous active mites were observed in the water treated sample but no activity was seen in the sample treated with the spray containing a 5% terpene mixture (carvone 5%) with citral forming 5% of the total spray.

Further Experiments on Eggs, Larvae and Pupae of Bluebottle Flies

This series was designed to investigate the effect of a spray formulation, according to the instant invention, to investigate the effect on bluebottle fly eggs, larvae (maggots), and pupae.

Bluebottle flies were maintained captive in an environmental chamber where they were fed and provided for. Eggs laid by the flies were carefully retrieved. In one experiment, 5 bluebottle fly eggs were placed on half a Whatman No. 50 filter in a Petri dish and 1 ml of the 5% terpene mixture (carvone 5%) with citral forming 5% of the total spray formulation was delivered onto the eggs, with a dropper, in order to coat them. In a parallel experiment, 5 bluebottle fly eggs were treated with water using the same method. In a further experiment, 12 bluebottle fly eggs were untreated. The eggs in all three batches were then incubated at 25° C.

None of the eggs from the treated group hatched, however, they did undergo a color change from white to brown as desiccation occurred between 24 and 48 hours. All the eggs from the other two groups hatched.

In a further series of experiments, fly larvae were obtained and treated with a spray according to the instant invention. Table 13 shows the results of exposing maggots to the 5% terpene mixture (carvone 5%) with citral forming 5% of the total spray. A sprayed water control experiment was also carried out.

TABLE 13

| Test Solution | Time after exposure (hours)/Apparent death rate (%) | | | | |
|---|---|---|---|---|---|
| | 0 | 0.5 | 2 | 4 | 24 |
| 5% Terpene spray (Carvone 5%) with Citral 5% <2 sec | 0 | 0 | 0 | 39 | 45 |
| Water control 1 sec | 0 | 0 | 0 | 0 | 0 |

From Table 13, it may be seen that the spray formulation containing 5% of the terpene mixture (including carvone 5%) with citral forming 5% of the total spray was moderately effective in killing maggots after a 2 second spray.

Maggots were subsequently maintained in an environmental chamber until they pupated. Within about 8 hours they were sprayed briefly with the spray formulation containing 5% of the terpene mixture (including carvone 5%) with citral forming 5% of the total shampoo. None subsequently hatched.

Formulation of an Alcohol Based Spray Containing Terpene Mixture With Citral

An alcoholic spray formulation, according to the present invention, was made using a base prepared by mixing the following:

| | |
|---|---|
| Alcohol base | 80.00% w/w |
| Surfactant (non-ionic) | 10.00% w/w |
| The active ingredients comprise:- | |
| Terpene Mixture (containing 5% carvone) | 5.00% w/w |
| Citral | 5.00% w/w |

Conveniently, the alcohol base is Denatured methylated sprit (95%) and the non-ionic surfactant is Polysorbate 80™, both obtained commercially.

The active ingredients are mixed into the alcoholic base to produce a clear pale yellow liquid spray solution with a somewhat pungent lemon and alcohol odor. The alcohol based spray formulation may be appropriate to the presentation of the instant invention in the treatment of mites and other infestations by terrestrial arthropods. Such a formulation is most likely to be applicable to uses in certain animals and in the environment, rather than for direct application onto human skin.

Comparative experiments were undertaken between the aqueous and alcohol based spray formulations of the instant invention, both containing 5% of the terpene mixture (including carvone 5%) with citral forming 5% of the total spray to determine their relative performance against crickets and locusts.

TABLE 14

| Insect and Treatment | Knock down | Death |
|---|---|---|
| Crickets-Aqueous spray | <30 seconds | <1 minute |
| Crickets-Alcoholic spray | <30 seconds | <1 minute |
| Locusts-Aqueous spray | <1.5 minutes | <5 minutes |
| Locusts-Alcoholic spray | <30 seconds | <2 minutes |

In these experiments, crickets and locusts were subjected to a single spray of about 2 seconds. The spray employed was a pump spray producing a fine mist and was directed at insects from a distance of not less than 20 cm and not more than 30 cm. No water control experiment was carried out.

From Table 14, it is interesting to note that, whilst crickets are equally susceptible to the aqueous and alcoholic formulations, the much larger and economically more threatening locust is more readily knocked down and more speedily killed by the alcoholic spray.

The nominal 'delivered amount' of active ingredients from the alcoholic spray was determined by the same method as that used for the aqueous spray and was found to be about 29 $\mu$m per sq. cm. However, it should be noted that, when atomized during spraying, considerable alcohol base is lost to the atmosphere. For instance, the notional spray area was 410 sq. cm, over 44% greater than that for the aqueous spray and it is likely that the true delivered amount of active ingredients is considerably higher. We contemplate the use of denatured methylated spirit (70%) and the use of a retarder. However, it should be noted that, in contradistinction to the aqueous spray, the alcoholic spray was able to knock down bees in 30 seconds and death ensued within 5 minutes.

The wax solvent properties of the alcoholic spray were investigated and compared to those of the aqueous shampoo concentrate using the coated glass slide method hereinbefore described.

TABLE 15

| Test Solution 2 minutes exposure | Total Weight of Beeswax | Percentage of beeswax remaining following exposure |
|---|---|---|
| 3% Terpene shampoo (Carvone 5%) with Citral 3%. | 0.2381 g | 94.49% |
| Undiluted | 0.2278 g | 97.36% |
| | | mean 95.92% |
| 5% Terpene spray (Carvone 5%) with Citral 5% | 0.0362 g | 96.13% |
| | 0.0209 g | 94.26% |
| | | mean 95.19% |

Table 15 shows the results obtained using this procedure with undiluted aqueous shampoo, according to the present invention, and containing a 3% terpene mixture (carvone 5%) with citral forming 3% of the total shampoo and also with an alcoholic spray containing 5% of the terpene mixture (including carvone 5%) with citral forming 5% of the total spray. For the purposes of this experiment, the spray formulation was used as a dip for the slide, as with the shampoo. Slides were immersed for 2 minutes then rinsed and dried at 40° C. for 20 minutes. No water control experiment was carried out. From Table 15, it will be apparent that the solvent effect of the aqueous and alcoholic solutions tested on insect derived wax, are similar.

Formulation of a Comb Dip Having a Water And Alcohol Base and Containing Terpene Mixture With Citral A dip formulation, for the immersion of combs to prevent the spread of pediculosis, according to the present invention, was made using a base prepared by mixing the following:

| | |
|---|---|
| Isopropyl alcohol | 25.00% w/w |
| Surfactant (non-ionic) | 12.50% w/w |
| Solubilizer | 7.50% w/w |
| Purified water (reverse osmosis water) | 49.00% w/w |
| The active ingredients comprise:- | |
| Terpene Mixture (containing carvone 5%) | 3.00% w/w |
| Citral | 3.00% w/w |

Conveniently, the alcohol component of the base may be isopropyl alcohol, the non-ionic surfactant may be polysorbate 80 and the solubilizer may be Solulan 98™, all obtained commercially.

The surfactant is dissolved in a quantity of cold water, with mixing, which is continued for 10 minutes. Then, during further mixing, are added the isopropyl alcohol and solubilizer. Mixing is continued for 15 minutes. With further mixing, the terpene mixture (including 5% carvone) is then added, followed by the citral. Mixing is continued for a further 20 minutes. The resultant product is a clear pale yellow liquid with a pleasing lemon and mildly alcoholic odor.

From the foregoing descriptions of the instant invention, it will be obvious to those skilled in the art that modifications, and changes may be made thereto without departing from the spirit and scope thereof and that the invention may thus be adapted without departing from it as defined in the following claims.

What is claimed is:

1. A pesticide to exterminate terrestrial arthropods comprising: as an active ingredient of the pesticide an arthropodicidally effective amount of a mixture of the terpene compounds redistilled limonene, beta-ionone, linalool, geraniol, eugenol and one of the terpenes selected from the group consisting of carvone and myrcene, wherein the ingredients are diluted in solution.

2. The pesticide of claim 1, said pesticide comprising the following terpene components in percent by volume given with respect to the active ingredient of the pesticide:

| | |
|---|---|
| redistilled limonene | 45%; |
| beta-ionone | 25% |
| linalool | 10% |
| geraniol | 10% |
| eugenol | 5%; and |
| one of the terpenes selected from the group consisting of carvone and myrcene | 5%. |

3. The pesticide of claim 2 having a concentration ranging from 1% to 50% by volume of said active ingredient.

4. The pesticide of claim 2 wherein citral is added to provide 0.5% to 20% by volume of citral in the final volume of the pesticide.

5. The pesticide of claim 1, wherein said solution is aqueous containing one of the forms of water selected from the group consisting of distilled water, water produced by reverse osmosis, and de-ionized water.

6. The pesticide of claim 5, wherein said aqueous solution is selected from the group consisting of:

a shampoo for application to human and animal hair;

an additive for the washing of laundry;

a lotion for application to human and animal skin;

a shampoo for application to carpets, curtains, upholstery and bedding mattresses;

a spray for use against infesting arthropods;

a drench or dip for application to animals or crops; and a gel for application to human and animal skin.

7. The pesticide of claim 6, wherein said aqueous formulations contain one or more of:

surfactants;

thickening agents and stabilizers;

conditioning shampoo agents;

pearlizing agents;

chelating/softening agents;

emollients;

bases;

builders;

gelling agents;

pH regulators;

solubilizers; and antimicrobial preservatives.

8. The pesticide of claim 5, having an initial pH adjusted to between 8 and 8.5.

9. The pesticide of claim 1, wherein said solution is an alcoholic solution.

10. The pesticide of claim 9, wherein said alcoholic solution is selected from the group consisting of:

a spray for use against infesting arthropods;

a drench or dip for application to animals or crops;

a gel for application to human and animal skin; and a arthropodicidal dip for the immersion of combs.

11. The pesticide of claim 10, wherein said alcoholic solution contains one or more of surfactants and solubilizers.

12. The pesticide of claim 6 or 10, wherein the concentrations of the terpene components and citral are:

(i) a total concentration of 2.50% by volume of said terpene components with 1.75% by volume citral added;

(ii) a total concentration of 3% by volume of said terpene components with 3% by volume citral added;

(iii) a total concentration of 5% by volume of said terpene components with 5% by volume citral added; of (iv) a total concentration of 10% by volume of said terpene components with 7% by volume citral added.

13. A method for manufacturing a pesticide for exterminating terrestrial arthropods comprising the step of mixing as active ingredient of the pesticide an arthropodicidally effective amount of the terpene compounds redistilled limonene, beta-ionene, linalool, geraniol, eugenol and one of the terpenes selected from the group consisting of carvone and myrcene, all in a solution containing a form of water selected from the group consisting of distilled water, water produced by reverse osmosis, and de-ionized water.

14. The method of claim 13, wherein said step of mixing said terpene compounds in the aqueous solution of distilled water or water produced by reverse osmosis or de-ionized water, comprises mixing said terpene compounds in the following percentages by volume of the active ingredient of said insecticide:

| | |
|---|---|
| redistilled limonene | 45%; |
| beta-ionone | 25%; |
| linalool | 10%; |
| geraniol | 10%; |
| eugenol | 5%; and |
| one of the terpenes selected from the group consisting of carvone and myrcene | 5%. |

15. The method of claim 14, wherein said step of mixing said terpenes in the aqueous solution includes forming a concentration of said active ingredient ranging from 1% to 50% by volume.

16. The method of claim 14, wherein said step of mixing said terpenes in the aqueous solution further includes the addition of the terpene aldehyde citral as an additional active ingredient.

17. The method of claim 16, wherein said step of mixing said terpene aldehyde citral in the aqueous solution includes providing a final concentration of said active ingredient ranging from 0.5% to 20% by weight of said active ingredient in the final volume of the pesticide.

18. The method of claim 17, wherein in said step of mixing said terpene compounds in said aqueous solution, the concentration of said active ingredient ranges from 2.0% to 10% by weight of said active ingredient in the final volume of the pesticide.

19. The method of claim 17, wherein in said step of mixing said terpene aldehyde citral in said aqueous solution, the final concentration of said active ingredient ranges from 1.75% to 7% by weight of said active ingredient in the final volume of the pesticide.

20. The method of claim 16, further comprising the step of adding at least one surfactant.

21. The method of claim 16, further comprising the step of adding thickening agents and stabilizers.

22. The method of claim 16, further comprising the step of adding conditioning shampoo agents.

23. The method of claim 16, further comprising the step of adding a pearlizing agent.

24. The method of claim 16, further comprising the step of adding a chelating/softening agent.

25. The method of claim 16, further comprising the step of adding emollients.

26. The method of claim 16, further comprising the step of adding at least one base.

27. The method of claim 16, further comprising the step of adding a builder.

28. The method of claim 11, further comprising the step of adding a gelling agent.

29. The method of claim 16, further comprising the step of adding a pH regulator.

30. The method of claim 16, further comprising the step of adding a solubilizer.

31. The method of claim 16, further comprising the step of adjusting the initial pH of said aqueous solution to between 8.0 and 8.5.

32. The method of claim 16, further comprising the step of adding an antimicrobial preservative to said aqueous solution.

33. A method for manufacturing a pesticide for exterminating terrestrial arthropods comprising the step of mixing as active ingredient of the pesticide an arthropodicidally effective amount of the terpene compounds redistilled limonene, beta-ionene, linalool, geraniol, eugenol and one of the terpenes selected from the group consisting of carvone and myrcene, all in an alcoholic solution.

34. The method of claim 33, wherein said step of mixing said terpene compounds in the alcoholic solution comprises mixing said terpene compounds in the following percentages by volume of the active ingredient of said insecticide:

| | |
|---|---|
| redistilled limonene | 45%; |
| beta-ionone | 25%; |
| linalool | 10%; |
| geraniol | 10%; |
| eugenol | 5%; and |
| one of the terpenes selected from the group consisting of carvone and myrcene | 5% |

35. The method of claim 34, wherein said step of mixing said terpenes in the alcoholic solution further includes the addition of the terpene aldehyde citral as an additional active ingredient.

36. The method of claim 34, wherein said step of mixing said terpene aldehyde citral in the alcoholic solution includes providing a final concentration of said active ingredient ranging from 0.5% to 20% by weight of said active ingredient in the final volume of the pesticide.

37. The method of claim 36, wherein in said step of mixing said terpene compounds in said alcoholic solution, the concentration of said active ingredient ranges from 2.0% to 10% by weight of said active ingredient in the final volume of the pesticide.

38. The method of claim 36, wherein in said step of mixing said terpene aldehyde citral in said alcoholic solution, the final concentration of said active ingredient ranges from 1.75% to 7% by weight of said active ingredient in the final volume of the pesticide.

39. The method of claim 35, further comprising the step of adding at least one surfactant.

40. The method of claim 35, further comprising the step of adding thickening agents and stabilizers.

41. The method of claim 35, further comprising the step of adding conditioning shampoo agents.

42. The method of claim 35, further comprising the step of adding an antimicrobial preservative to said alcoholic solution.

* * * * *

UNITED STATES PATENT AND TRADEMARK OFFICE
CERTIFICATE OF CORRECTION

PATENT NO. : 6,130,253
DATED : October 10, 2000
INVENTOR(S) : Lanny Udell Franklin, Gary David Cunnington, and David E. Young It is certified that error appears in the above-indentified patent and that said Letters Patent is hereby corrected as shown below:

In claim 12, line 9, "of" should read -- or --.

Signed and Sealed this

Twenty-ninth Day of May, 2001

Attest:

NICHOLAS P. GODICI

*Attesting Officer*    *Acting Director of the United States Patent and Trademark Office*

UNITED STATES PATENT AND TRADEMARK OFFICE
CERTIFICATE OF CORRECTION

PATENT NO. : 6,130,253
DATED : October 10, 2000
INVENTOR(S) : Lanny Udell Franklin, Gary David Cunnington and David E. Young It is certified that error appears in the above-identified patent and that said Letters Patent is hereby corrected as shown below:

<u>Column 44,</u>
Line 56, "of" should read -- or --.

Signed and Sealed this

Third Day of December, 2002

JAMES E. ROGAN
*Director of the United States Patent and Trademark Office*